United States Patent [19]
Crosby et al.

[11] Patent Number: 5,639,663
[45] Date of Patent: Jun. 17, 1997

[54] BIFUNCTIONAL GENETIC MARKERS

[75] Inventors: William L. Crosby; Raju S. Datla; Joe K. Hammerlindl; Gopalan Selvaraj, all of Saskatoon, Canada

[73] Assignee: National Research Council of Canada, Ottawa, Canada

[21] Appl. No.: 122,520

[22] PCT Filed: Mar. 30, 1992

[86] PCT No.: PCT/CA92/00139

§ 371 Date: Jan. 21, 1994

§ 102(e) Date: Jan. 21, 1994

[87] PCT Pub. No.: WO92/17593

PCT Pub. Date: Oct. 15, 1992

Related U.S. Application Data

[63] Continuation-in-part of Ser. No. 676,432, Mar. 28, 1991, abandoned.

[51] Int. Cl.$^6$ ..................................................... C12N 15/62
[52] U.S. Cl. .................. 435/320.1; 435/69.7; 536/23.2; 536/23.4; 536/24.3
[58] Field of Search ................................ 435/8, 18, 69.1, 435/69.7, 69.8, 172.3, 300.1; 536/23.2, 23.4, 24.3

[56] References Cited

FOREIGN PATENT DOCUMENTS 0302381  2/1989  European Pat. Off. .

OTHER PUBLICATIONS

Reiss et al. (1984) The EMBO Journal vol. 3: pp. 3317–3322.
Cohen in The Enzymes (Boyer) Academic Press, NY, 1970, pp. 147–150 178–185, and 194–197.
Richardson (1981) Advances in Protein Chemistry vol. 34: pp. 253–339.
Jobling et al. (1987) Nature vol. 325: pp. 623–624.
Vaeck et al (1987) Nature vol. 328, pp. 33–37.
Teeri et al (1986) The EMBO Journal vol. 5(8): pp. 1755–1760.
Jefferson et al. (1987) The EMBO Journal vol. 6(13): pp. 3901–3907.
Silhavy et al (1985) Microbiological Reviews vol. 49(4): pp. 398–418.

*Primary Examiner*—Che S. Chereskin
*Attorney, Agent, or Firm*—J. Wayne Anderson

[57] ABSTRACT

Genetic markers of this invention provide a biochemically assayable reporter activity and a conditionally selectable growth advantage. They comprise a first gene which encodes a product whose activity can be assdyed biochemically e.g., β-glucuronidase, to a second gene which confers a conditional growth advantage such as antibiotic resistance in a transformed cell (e.g., neomycin phosphotransferase-II). The marker genes and their translational products are stable in cells. The genetic markers provide for the positive genetic selection and the biochemical and histochemical screening of transformed cells. They can be used as probes for identification and isolation of novel genetic regulatory elements, such as promoters, and the genes they regulate.

15 Claims, 9 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..123

( x i ) SEQUENCE DESCRIPTION: SEQ ID NO:1:

```
ATG  AAC  TTC  GGT  GAA  AAA  CCG  CGC  AGG  GAG  GCA  AAC  AAT  GAA  TCA  ACA      48
Met  Asn  Phe  Gly  Glu  Lys  Pro  Arg  Arg  Glu  Ala  Asn  Asn  Glu  Ser  Thr
 1                  5                        10                       15

ACT  CTC  CTG  GCG  CAC  CAT  CGT  CGG  CTA  CAG  CCT  CGG  GAA  TTG  CTA  CCG      96
Thr  Leu  Leu  Ala  His  His  Arg  Arg  Leu  Gln  Pro  Arg  Glu  Leu  Leu  Pro
                    20                       25                       30

AGC  TCG  AGC  TTG  GAT  GGA  TTG  CAC  GCA                                         123
Ser  Ser  Ser  Leu  Asp  Gly  Leu  His  Ala
                    35                       40
```

( 2 ) INFORMATION FOR SEQ ID NO:2:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asn  Phe  Gly  Glu  Lys  Pro  Arg  Arg  Glu  Ala  Asn  Asn  Glu  Ser  Thr
 1                  5                        10                       15

Thr  Leu  Leu  Ala  His  His  Arg  Arg  Leu  Gln  Pro  Arg  Glu  Leu  Leu  Pro
                    20                       25                       30
```

```
Ser  Ser  Ser  Leu  Asp  Gly  Leu  His  Ala
          35                      40
```

(2) INFORMATION FOR SEQ ID NO:3:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..42

(xi) SEQUENCE DESCRIPTION: SEQ ID NO:3:

```
ATG  AAC  TTC  GGT  GAA  AAA  CCG  CAG  CAG  GGA  GGC  AAA  CAA  TGA  ATCAACA       49
Met  Asn  Phe  Gly  Glu  Lys  Pro  Gln  Gln  Gly  Gly  Lys  Gln   *
 1              5                           10

ACTCTCCTGG  CGCACCATCG  TCGGCTACAG  CCTCGGGAAT  TGCTACCGAG  CTCGAGCTTG             109

GATGGATTGC  ACGCA                                                                   124
```

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Asn  Phe  Gly  Glu  Lys  Pro  Gln  Gln  Gly  Gly  Lys  Gln
 1              5                           10
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GAAAACCGC  GCAGGGAG                                                                  18
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CCGGATCCAA  ATGGAAGACG                                                               20
```

(2) INFORMATION FOR SEQ ID NO:7:

(i) SEQUENCE CHARACTERISTICS:
        (A) LENGTH: 26 base pairs
        (B) TYPE: nucleic acid (C) STRANDEDNESS: single
(D) TOPOLOGY: linear (ii) MOLECULE TYPE: cDNA (xi) SEQUENCE DESCRIPTION: SEQ ID NO:7:

GGAGCTCGGC AATTTGGACT TTCCGC 26

(2) INFORMATION FOR SEQ ID NO:8:

(i) SEQUENCE CHARACTERISTICS:
 (A) LENGTH: 2445 base pairs
 (B) TYPE: nucleic acid
 (C) STRANDEDNESS: single
 (D) TOPOLOGY: linear (ii) MOLECULE TYPE: cDNA (ix) FEATURE:
 (A) NAME/KEY: CDS
 (B) LOCATION: 1..2445

(ix) FEATURE:
 (A) NAME/KEY: misc_feature
 (B) LOCATION: 1652..1659
 (D) OTHER INFORMATION: /function="SacI site"

(xi) SEQUENCE DESCRIPTION: SEQ ID NO:8:

| | | | | | | | | | | | | | | | | |
|---|---|---|---|---|---|---|---|---|---|---|---|---|---|---|---|---|
| ATG | GAA | GAC | GCC | AAA | AAC | ATA | AAG | AAA | GGC | CCG | GCG | CCA | TTC | TAT | CCT | 48 |
| Met | Glu | Asp | Ala | Lys | Asn | Ile | Lys | Lys | Gly | Pro | Ala | Pro | Phe | Tyr | Pro | |
| 1 | | | | 5 | | | | | 10 | | | | | 15 | | |
| CTA | GAG | GAT | GGA | ACC | GCT | GGA | GAG | CAA | CTG | CAT | AAG | GCT | ATG | AAG | AGA | 96 |
| Leu | Glu | Asp | Gly | Thr | Ala | Gly | Glu | Gln | Leu | His | Lys | Ala | Met | Lys | Arg | |
| | | | 20 | | | | | 25 | | | | | 30 | | | |
| TAC | GCC | CTG | GTT | CCT | GGA | ACA | ATT | GCT | TTT | ACA | GAT | GCA | CAT | ATC | GAG | 144 |
| Tyr | Ala | Leu | Val | Pro | Gly | Thr | Ile | Ala | Phe | Thr | Asp | Ala | His | Ile | Glu | |
| | | 35 | | | | | 40 | | | | | 45 | | | | |
| GTG | AAC | ATC | ACG | TAC | GCG | GAA | TAC | TTC | GAA | ATG | TCC | GTT | CGG | TTG | GCA | 192 |
| Val | Asn | Ile | Thr | Tyr | Ala | Glu | Tyr | Phe | Glu | Met | Ser | Val | Arg | Leu | Ala | |
| | 50 | | | | | 55 | | | | | 60 | | | | | |
| GAA | GCT | ATG | AAA | CGA | TAT | GGG | CTG | AAT | ACA | AAT | CAC | AGA | ATC | GTC | GTA | 240 |
| Glu | Ala | Met | Lys | Arg | Tyr | Gly | Leu | Asn | Thr | Asn | His | Arg | Ile | Val | Val | |
| 65 | | | | | 70 | | | | | 75 | | | | | 80 | |
| TGC | AGT | GAA | AAC | TCT | CTT | CAA | TTC | TTT | ATG | CCG | GTG | TTG | GGC | GCG | TTA | 288 |
| Cys | Ser | Glu | Asn | Ser | Leu | Gln | Phe | Phe | Met | Pro | Val | Leu | Gly | Ala | Leu | |
| | | | | 85 | | | | | 90 | | | | | 95 | | |
| TTT | ATC | GGA | GTT | GCA | GTT | GCG | CCC | GCG | AAC | GAC | ATT | TAT | AAT | GAA | CGT | 336 |
| Phe | Ile | Gly | Val | Ala | Val | Ala | Pro | Ala | Asn | Asp | Ile | Tyr | Asn | Glu | Arg | |
| | | | 100 | | | | | 105 | | | | | 110 | | | |
| GAA | TTG | CTC | AAC | AGT | ATG | AAC | ATT | TCG | CAG | CCT | ACC | GTA | GTG | TTT | GTT | 384 |
| Glu | Leu | Leu | Asn | Ser | Met | Asn | Ile | Ser | Gln | Pro | Thr | Val | Val | Phe | Val | |
| | | 115 | | | | | 120 | | | | | 125 | | | | |
| TCC | AAA | AAG | GGG | TTG | CAA | AAA | ATT | TTG | AAC | GTG | CAA | AAA | AAA | TTA | CCA | 432 |
| Ser | Lys | Lys | Gly | Leu | Gln | Lys | Ile | Leu | Asn | Val | Gln | Lys | Lys | Leu | Pro | |
| | 130 | | | | | 135 | | | | | 140 | | | | | |
| ATA | ATC | CAG | AAA | ATT | ATT | ATC | ATG | GAT | TCT | AAA | ACG | GAT | TAC | CAG | GGA | 480 |
| Ile | Ile | Gln | Lys | Ile | Ile | Ile | Met | Asp | Ser | Lys | Thr | Asp | Tyr | Gln | Gly | |
| 145 | | | | | 150 | | | | | 155 | | | | | 160 | |
| TTT | CAG | TCG | ATG | TAC | ACG | TTC | GTC | ACA | TCT | CAT | CTA | CCT | CCC | GGT | TTT | 528 |
| Phe | Gln | Ser | Met | Tyr | Thr | Phe | Val | Thr | Ser | His | Leu | Pro | Pro | Gly | Phe | |
| | | | | 165 | | | | | 170 | | | | | 175 | | |
| AAT | GAA | TAC | GAT | TTT | GTA | CCA | GAG | TCC | TTT | GAT | CGT | GAC | AAA | ACA | ATT | 576 |
| Asn | Glu | Tyr | Asp | Phe | Val | Pro | Glu | Ser | Phe | Asp | Arg | Asp | Lys | Thr | Ile | |
| | | | 180 | | | | | 185 | | | | | 190 | | | |
| GCA | CTG | ATA | ATG | AAT | TCC | TCT | GGA | TCT | ACT | GGG | TTA | CCT | AAG | GGT | GTG | 624 |

|     |     |     |     |     |     |     |     |     |     |     |     |     |     |     |
| --- | --- | --- | --- | --- | --- | --- | --- | --- | --- | --- | --- | --- | --- | --- |
| Ala | Leu | Ile | Met | Asn | Ser | Ser | Gly | Ser | Thr | Gly | Leu | Pro | Lys | Gly | Val |
|     |     | 195 |     |     |     |     | 200 |     |     |     |     | 205 |     |     |     |

| GCC | CTT | CCG | CAT | AGA | ACT | GCC | TGC | GTC | AGA | TTC | TCG | CAT | GCC | AGA | GAT | 672 |
| --- | --- | --- | --- | --- | --- | --- | --- | --- | --- | --- | --- | --- | --- | --- | --- | --- |
| Ala | Leu | Pro | His | Arg | Thr | Ala | Cys | Val | Arg | Phe | Ser | His | Ala | Arg | Asp |     |
|     | 210 |     |     |     |     | 215 |     |     |     |     | 220 |     |     |     |     |     |
| CCT | ATT | TTT | GGC | AAT | CAA | ATC | ATT | CCG | GAT | ACT | GCG | ATT | TTA | AGT | GTT | 720 |
| Pro | Ile | Phe | Gly | Asn | Gln | Ile | Ile | Pro | Asp | Thr | Ala | Ile | Leu | Ser | Val |     |
| 225 |     |     |     |     | 230 |     |     |     |     | 235 |     |     |     |     | 240 |     |
| GTT | CCA | TTC | CAT | CAC | GGT | TTT | GGA | ATG | TTT | ACT | ACA | CTC | GGA | TAT | TTG | 768 |
| Val | Pro | Phe | His | His | Gly | Phe | Gly | Met | Phe | Thr | Thr | Leu | Gly | Tyr | Leu |     |
|     |     |     |     | 245 |     |     |     |     | 250 |     |     |     |     | 255 |     |     |
| ATA | TGT | GGA | TTT | CGA | GTC | GTC | TTA | ATG | TAT | AGA | TTT | GAA | GAA | GAG | CTG | 816 |
| Ile | Cys | Gly | Phe | Arg | Val | Val | Leu | Met | Tyr | Arg | Phe | Glu | Glu | Glu | Leu |     |
|     |     |     | 260 |     |     |     |     | 265 |     |     |     |     | 270 |     |     |     |
| TTT | TTA | CGA | TCC | CTT | CAG | GAT | TAC | AAA | ATT | CAA | AGT | GCG | TTG | CTA | GTA | 864 |
| Phe | Leu | Arg | Ser | Leu | Gln | Asp | Tyr | Lys | Ile | Gln | Ser | Ala | Leu | Leu | Val |     |
|     |     | 275 |     |     |     |     | 280 |     |     |     |     | 285 |     |     |     |     |
| CCA | ACC | CTA | TTT | TCA | TTC | TTC | GCC | AAA | AGC | ACT | CTG | ATT | GAC | AAA | TAC | 912 |
| Pro | Thr | Leu | Phe | Ser | Phe | Phe | Ala | Lys | Ser | Thr | Leu | Ile | Asp | Lys | Tyr |     |
|     | 290 |     |     |     |     | 295 |     |     |     |     | 300 |     |     |     |     |     |
| GAT | TTA | TCT | AAT | TTA | CAC | GAA | ATT | GCT | TCT | GGG | GGC | GCA | CCT | CTT | TCG | 960 |
| Asp | Leu | Ser | Asn | Leu | His | Glu | Ile | Ala | Ser | Gly | Gly | Ala | Pro | Leu | Ser |     |
| 305 |     |     |     |     | 310 |     |     |     |     | 315 |     |     |     |     | 320 |     |
| AAA | GAA | GTC | GGG | GAA | GCG | GTT | GCA | AAA | CGC | TTC | CAT | CTT | CCA | GGG | ATA | 1008 |
| Lys | Glu | Val | Gly | Glu | Ala | Val | Ala | Lys | Arg | Phe | His | Leu | Pro | Gly | Ile |     |
|     |     |     |     | 325 |     |     |     |     | 330 |     |     |     |     | 335 |     |     |
| CGA | CAA | GGA | TAT | GGG | CTC | ACT | GAG | ACT | ACA | TCA | GCT | ATT | CTG | ATT | ACA | 1056 |
| Arg | Gln | Gly | Tyr | Gly | Leu | Thr | Glu | Thr | Thr | Ser | Ala | Ile | Leu | Ile | Thr |     |
|     |     |     | 340 |     |     |     |     | 345 |     |     |     |     | 350 |     |     |     |
| CCC | GAG | GGG | GAT | GAT | AAA | CCG | GGC | GCG | GTC | GGT | AAA | GTT | GTT | CCA | TTT | 1104 |
| Pro | Glu | Gly | Asp | Asp | Lys | Pro | Gly | Ala | Val | Gly | Lys | Val | Val | Pro | Phe |     |
|     |     | 355 |     |     |     |     | 360 |     |     |     |     | 365 |     |     |     |     |
| TTT | GAA | GCG | AAG | GTT | GTG | GAT | CTG | GAT | ACC | GGG | AAA | ACG | CTG | GGC | GTT | 1152 |
| Phe | Glu | Ala | Lys | Val | Val | Asp | Leu | Asp | Thr | Gly | Lys | Thr | Leu | Gly | Val |     |
|     | 370 |     |     |     |     | 375 |     |     |     |     | 380 |     |     |     |     |     |
| AAT | CAG | AGA | GGC | GAA | TTA | TGT | GTC | AGA | GGA | CCT | ATG | ATT | ATG | TCC | GGT | 1200 |
| Asn | Gln | Arg | Gly | Glu | Leu | Cys | Val | Arg | Gly | Pro | Met | Ile | Met | Ser | Gly |     |
| 385 |     |     |     |     | 390 |     |     |     |     | 395 |     |     |     |     | 400 |     |
| TAT | GTA | AAC | AAT | CCG | GAA | GCG | ACC | AAC | GCC | TTG | ATT | GAC | AAG | GAT | GGA | 1248 |
| Tyr | Val | Asn | Asn | Pro | Glu | Ala | Thr | Asn | Ala | Leu | Ile | Asp | Lys | Asp | Gly |     |
|     |     |     |     | 405 |     |     |     |     | 410 |     |     |     |     | 415 |     |     |
| TGG | CTA | CAT | TCT | GGA | GAC | ATA | GCT | TAC | TGG | GAC | GAA | GAC | GAA | CAC | TTC | 1296 |
| Trp | Leu | His | Ser | Gly | Asp | Ile | Ala | Tyr | Trp | Asp | Glu | Asp | Glu | His | Phe |     |
|     |     |     | 420 |     |     |     |     | 425 |     |     |     |     | 430 |     |     |     |
| TTC | ATA | GTT | GAC | CGC | TTG | AAG | TCT | TTA | ATT | AAA | TAC | AAA | GGA | TAT | CAG | 1344 |
| Phe | Ile | Val | Asp | Arg | Leu | Lys | Ser | Leu | Ile | Lys | Tyr | Lys | Gly | Tyr | Gln |     |
|     |     | 435 |     |     |     |     | 440 |     |     |     |     | 445 |     |     |     |     |
| GTG | GCC | CCC | GCT | GAA | TTG | GAA | TCG | ATA | TTG | TTA | CAA | CAC | CCC | AAC | ATC | 1392 |
| Val | Ala | Pro | Ala | Glu | Leu | Glu | Ser | Ile | Leu | Leu | Gln | His | Pro | Asn | Ile |     |
|     | 450 |     |     |     |     | 455 |     |     |     |     | 460 |     |     |     |     |     |
| TTC | GAC | GCG | GGC | GTG | GCA | GGT | CTT | CCC | GAC | GAT | GAC | GCC | GGT | GAA | CTT | 1440 |
| Phe | Asp | Ala | Gly | Val | Ala | Gly | Leu | Pro | Asp | Asp | Asp | Ala | Gly | Glu | Leu |     |
| 465 |     |     |     |     | 470 |     |     |     |     | 475 |     |     |     |     | 480 |     |
| CCC | GCC | GCC | GTT | GTT | GTT | TTG | GAG | CAC | GGA | AAG | ACG | ATG | ACG | GAA | AAA | 1488 |
| Pro | Ala | Ala | Val | Val | Val | Leu | Glu | His | Gly | Lys | Thr | Met | Thr | Glu | Lys |     |
|     |     |     |     | 485 |     |     |     |     | 490 |     |     |     |     | 495 |     |     |
| GAG | ATC | GTG | GAT | TAC | GTC | GCC | AGT | CAA | GTA | ACA | ACC | GCG | AAA | AAG | TTG | 1536 |
| Glu | Ile | Val | Asp | Tyr | Val | Ala | Ser | Gln | Val | Thr | Thr | Ala | Lys | Lys | Leu |     |
|     |     |     | 500 |     |     |     |     | 505 |     |     |     |     | 510 |     |     |     |
| CGC | GGA | GGA | GTT | GTG | TTT | GTG | GAC | GAA | GTA | CCG | AAA | GGT | CTT | ACC | GGA | 1584 |

|     |     |     |     |     |     |     |     |     |     |     |     |     |     |     |
|-----|-----|-----|-----|-----|-----|-----|-----|-----|-----|-----|-----|-----|-----|-----|
| Arg | Gly | Gly | Val | Val | Phe | Val | Asp | Glu | Val | Pro | Lys | Gly | Leu | Thr | Gly |
|     |     | 515 |     |     |     |     | 520 |     |     |     | 525 |     |     |     |

| AAA | CTC | GAC | GCA | AGA | AAA | ATC | AGA | GAG | ATC | CTC | ATA | AAG | GCC | AAG | AAG | 1632 |
|-----|-----|-----|-----|-----|-----|-----|-----|-----|-----|-----|-----|-----|-----|-----|-----|------|
| Lys | Leu | Asp | Ala | Arg | Lys | Ile | Arg | Glu | Ile | Leu | Ile | Lys | Ala | Lys | Lys |      |
|     |     | 530 |     |     |     | 535 |     |     |     |     | 540 |     |     |     |     |      |

| GGC | GGA | AAG | TCC | AAA | TTG | CCG | AGC | TCG | AGC | TTG | GAT | GGA | TTG | CAC | GCA | 1680 |
| Gly | Gly | Lys | Ser | Lys | Leu | Pro | Ser | Ser | Ser | Leu | Asp | Gly | Leu | His | Ala |      |
| 545 |     |     |     | 550 |     |     |     |     | 555 |     |     |     |     | 560 |     |      |

| GGT | TCT | CCG | GCC | GCT | TGG | GTG | GAG | AGG | CTA | TTC | GGC | TAT | GAC | TGG | GCA | 1728 |
| Gly | Ser | Pro | Ala | Ala | Trp | Val | Glu | Arg | Leu | Phe | Gly | Tyr | Asp | Trp | Ala |      |
|     |     |     |     | 565 |     |     |     |     | 570 |     |     |     |     | 575 |     |      |

| CAA | CAG | ACA | ATC | GGC | TGC | TCT | GAT | GCC | GCC | GTG | TTC | CGG | CTG | TCA | GCG | 1776 |
| Gln | Gln | Thr | Ile | Gly | Cys | Ser | Asp | Ala | Ala | Val | Phe | Arg | Leu | Ser | Ala |      |
|     |     |     | 580 |     |     |     |     | 585 |     |     |     |     | 590 |     |     |      |

| CAG | GGG | CGC | CCG | GTT | CTT | TTT | GTC | AAG | ACC | GAC | CTG | TCC | GGT | GCC | CTG | 1824 |
| Gln | Gly | Arg | Pro | Val | Leu | Phe | Val | Lys | Thr | Asp | Leu | Ser | Gly | Ala | Leu |      |
|     |     | 595 |     |     |     |     | 600 |     |     |     |     | 605 |     |     |     |      |

| AAT | GAA | CTG | CAG | GAC | GAG | GCA | GCG | CGG | CTA | TCG | TGG | CTG | GCC | ACG | ACG | 1872 |
| Asn | Glu | Leu | Gln | Asp | Glu | Ala | Ala | Arg | Leu | Ser | Trp | Leu | Ala | Thr | Thr |      |
|     | 610 |     |     |     |     | 615 |     |     |     |     | 620 |     |     |     |     |      |

| GGC | GTT | CCT | TGC | GCA | GCT | GTG | CTC | GAC | GTT | GTC | ACT | GAA | GCG | GGA | AGG | 1920 |
| Gly | Val | Pro | Cys | Ala | Ala | Val | Leu | Asp | Val | Val | Thr | Glu | Ala | Gly | Arg |      |
| 625 |     |     |     |     | 630 |     |     |     |     | 635 |     |     |     |     | 640 |      |

| GAC | TGG | CTG | CTA | TTG | GGC | GAA | GTG | CCG | GGG | CAG | GAT | CTC | CTG | TCA | TCT | 1968 |
| Asp | Trp | Leu | Leu | Leu | Gly | Glu | Val | Pro | Gly | Gln | Asp | Leu | Leu | Ser | Ser |      |
|     |     |     |     | 645 |     |     |     |     | 650 |     |     |     |     | 655 |     |      |

| CAC | CTT | GCT | CCT | GCC | GAG | AAA | GTA | TCC | ATC | ATG | GCT | GAT | GCA | ATG | CGG | 2016 |
| His | Leu | Ala | Pro | Ala | Glu | Lys | Val | Ser | Ile | Met | Ala | Asp | Ala | Met | Arg |      |
|     |     |     | 660 |     |     |     |     | 665 |     |     |     |     | 670 |     |     |      |

| CGG | CTG | CAT | ACG | CTT | GAT | CCG | GCT | ACC | TGC | CCA | TTC | GAC | CAC | CAA | GCG | 2064 |
| Arg | Leu | His | Thr | Leu | Asp | Pro | Ala | Thr | Cys | Pro | Phe | Asp | His | Gln | Ala |      |
|     |     | 675 |     |     |     |     | 680 |     |     |     |     | 685 |     |     |     |      |

| AAA | CAT | CGC | ATC | GAG | CGA | GCA | CGT | ACT | CGG | ATG | GAA | GCC | GGT | CTT | GTC | 2112 |
| Lys | His | Arg | Ile | Glu | Arg | Ala | Arg | Thr | Arg | Met | Glu | Ala | Gly | Leu | Val |      |
|     | 690 |     |     |     |     | 695 |     |     |     |     | 700 |     |     |     |     |      |

| GAT | CAG | GAT | GAT | CTG | GAC | GAA | GAG | CAT | CAG | GGG | CTC | GCG | CCA | GCC | GAA | 2160 |
| Asp | Gln | Asp | Asp | Leu | Asp | Glu | Glu | His | Gln | Gly | Leu | Ala | Pro | Ala | Glu |      |
| 705 |     |     |     |     | 710 |     |     |     |     | 715 |     |     |     |     | 720 |      |

| CTG | TTC | GCC | AGG | CTC | AAG | GCG | CGC | ATG | CCC | GAC | GGC | GAG | GAT | CTC | GTC | 2208 |
| Leu | Phe | Ala | Arg | Leu | Lys | Ala | Arg | Met | Pro | Asp | Gly | Glu | Asp | Leu | Val |      |
|     |     |     |     | 725 |     |     |     |     | 730 |     |     |     |     | 735 |     |      |

| GTG | ACC | CAT | GGC | GAT | GCC | TGC | TTG | CCG | AAT | ATC | ATG | GTG | GAA | AAT | GGC | 2256 |
| Val | Thr | His | Gly | Asp | Ala | Cys | Leu | Pro | Asn | Ile | Met | Val | Glu | Asn | Gly |      |
|     |     |     | 740 |     |     |     |     | 745 |     |     |     |     | 750 |     |     |      |

| CGC | TTT | TCT | GGA | TTC | ATC | GAC | TGT | GGC | CGG | CTG | GGT | GTG | GCG | GAC | CGC | 2304 |
| Arg | Phe | Ser | Gly | Phe | Ile | Asp | Cys | Gly | Arg | Leu | Gly | Val | Ala | Asp | Arg |      |
|     |     | 755 |     |     |     |     | 760 |     |     |     |     | 765 |     |     |     |      |

| TAT | CAG | GAC | ATA | GCG | TTG | GCT | ACC | CGT | GAT | ATT | GCT | GAA | GAG | CTT | GGC | 2352 |
| Tyr | Gln | Asp | Ile | Ala | Leu | Ala | Thr | Arg | Asp | Ile | Ala | Glu | Glu | Leu | Gly |      |
|     | 770 |     |     |     |     | 775 |     |     |     |     | 780 |     |     |     |     |      |

| GGC | GAA | TGG | GCT | GAC | CGC | TTC | CTC | GTG | CTT | TAC | GGT | ATC | GCC | GCT | CCC | 2400 |
| Gly | Glu | Trp | Ala | Asp | Arg | Phe | Leu | Val | Leu | Tyr | Gly | Ile | Ala | Ala | Pro |      |
| 785 |     |     |     |     | 790 |     |     |     |     | 795 |     |     |     |     | 800 |      |

| GAT | TCG | CAG | CGC | ATC | GCC | TTC | TAT | CGC | CTT | CTT | GAC | GAG | TTC | TTC |     | 2445 |
| Asp | Ser | Gln | Arg | Ile | Ala | Phe | Tyr | Arg | Leu | Leu | Asp | Glu | Phe | Phe |     |      |
|     |     |     |     | 805 |     |     |     |     | 810 |     |     |     |     | 815 |     |      |

( 2 ) INFORMATION FOR SEQ ID NO:9:

( i ) SEQUENCE CHARACTERISTICS:
        ( A ) LENGTH: 815 amino acids ( B ) TYPE: amino acid
( D ) TOPOLOGY: linear ( i i ) MOLECULE TYPE: protein ( x i ) SEQUENCE DESCRIPTION: SEQ ID NO:9:

```
Met Glu Asp Ala Lys Asn Ile Lys Lys Gly Pro Ala Pro Phe Tyr Pro
  1               5                  10                  15
Leu Glu Asp Gly Thr Ala Gly Glu Gln Leu His Lys Ala Met Lys Arg
                 20                  25                  30
Tyr Ala Leu Val Pro Gly Thr Ile Ala Phe Thr Asp Ala His Ile Glu
             35                  40                  45
Val Asn Ile Thr Tyr Ala Glu Tyr Phe Glu Met Ser Val Arg Leu Ala
         50                  55                  60
Glu Ala Met Lys Arg Tyr Gly Leu Asn Thr Asn His Arg Ile Val Val
 65                  70                  75                  80
Cys Ser Glu Asn Ser Leu Gln Phe Phe Met Pro Val Leu Gly Ala Leu
                 85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
            115                 120                 125
Ser Lys Lys Gly Leu Gln Lys Ile Leu Asn Val Gln Lys Lys Leu Pro
    130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
            195                 200                 205
Ala Leu Pro His Arg Thr Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
    275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
```

-continued

| 385 | | | | | 390 | | | | | 395 | | | | | 400 |
|---|---|---|---|---|---|---|---|---|---|---|---|---|---|---|---|

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
                420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540

Gly Gly Lys Ser Lys Leu Pro Ser Ser Ser Leu Asp Gly Leu His Ala
545                 550                 555                 560

Gly Ser Pro Ala Ala Trp Val Glu Arg Leu Phe Gly Tyr Asp Trp Ala
                565                 570                 575

Gln Gln Thr Ile Gly Cys Ser Asp Ala Ala Val Phe Arg Leu Ser Ala
            580                 585                 590

Gln Gly Arg Pro Val Leu Phe Val Lys Thr Asp Leu Ser Gly Ala Leu
        595                 600                 605

Asn Glu Leu Gln Asp Glu Ala Ala Arg Leu Ser Trp Leu Ala Thr Thr
    610                 615                 620

Gly Val Pro Cys Ala Ala Val Leu Asp Val Val Thr Glu Ala Gly Arg
625                 630                 635                 640

Asp Trp Leu Leu Leu Gly Glu Val Pro Gly Gln Asp Leu Leu Ser Ser
                645                 650                 655

His Leu Ala Pro Ala Glu Lys Val Ser Ile Met Ala Asp Ala Met Arg
            660                 665                 670

Arg Leu His Thr Leu Asp Pro Ala Thr Cys Pro Phe Asp His Gln Ala
        675                 680                 685

Lys His Arg Ile Glu Arg Ala Arg Thr Arg Met Glu Ala Gly Leu Val
    690                 695                 700

Asp Gln Asp Asp Leu Asp Glu Glu His Gln Gly Leu Ala Pro Ala Glu
705                 710                 715                 720

Leu Phe Ala Arg Leu Lys Ala Arg Met Pro Asp Gly Glu Asp Leu Val
                725                 730                 735

Val Thr His Gly Asp Ala Cys Leu Pro Asn Ile Met Val Glu Asn Gly
            740                 745                 750

Arg Phe Ser Gly Phe Ile Asp Cys Gly Arg Leu Gly Val Ala Asp Arg
        755                 760                 765

Tyr Gln Asp Ile Ala Leu Ala Thr Arg Asp Ile Ala Glu Glu Leu Gly
    770                 775                 780

Gly Glu Trp Ala Asp Arg Phe Leu Val Leu Tyr Gly Ile Ala Ala Pro
785                 790                 795                 800

Asp Ser Gln Arg Ile Ala Phe Tyr Arg Leu Leu Asp Glu Phe Phe
                805                 810                 815

BIFUNCTIONAL GENETIC MARKERS

CROSS-REFERENCE TO RELATED APPLICATION

This application is a Continuation-in Part of prior U.S. application Ser. No. 07/676,432, filed 28 Mar. 1991, now Abandoned.

BACKGROUND OF THE INVENTION

Transcriptional and translational fusions to reporter genes whose products can be easily assayed offer powerful approaches to studying gene structure, expression, regulation, gene product assembly, transport and compartmentalization (Rosenberg et al., Science 222:734–739, 1983; Bonnerot et al., Proc. Nat. Acad. Sci. U.S.A. 84:6795–6799, 1987; Finnegan et al., The Plant Cell 1:757–764, 1989). Some of these gene fusions have been applied in more wide-ranging studies such as discerning cell lineage during development and purifying gene products (Germino et al., Proc. Nat. Acad. Sci. U.S.A. 80:6848–6852, 1983; Silhavy and Beckwith, Microbiol Rev. 49:398–418, 1985; Scholtissek and Grosse, Gene 62:55–64, 1988). Pioneered with E. coli β-galactosidase (lacZ), gene fusions have been adapted to other organisms including yeast, animals and plants. While transcriptional fusions might be construed as straightforward, translational fusions require reporters which can function despite covalent addition of extraneous polypeptides to their amino- or carboxy-terminus.

Some genetic markers impart a selectable phenotype such as antibiotic resistance while other markers specify an enzymatic reporter activity for which there is a colorimetric or luminescence assay, making them suitable in combination for selection and screening. Single genetic markers which provide both of these features would be particularly useful.

The following references constitute background art:

Barnes, W. M. (1990) Proc. Natl. Acad. Sci. U.S.A. 87 9183–9187.
Raju, S. S. et al. (1990) J. of Cellular Biochemistry supp. 14E: UCLA symposia on molecular and cellular biology p. 279, abstr R115.
WO-A-8402913 Monsanto Company, 2 Aug., 1984 pp. 52–53.
Koncz, C. (1989) Proc. Natl. Acad. Sci. U.S.A. 86, pp. 8467–8471.
Restrepo et al. 1990 The Plant Cell 2:987–998.

SUMMARY OF THE INVENTION

This invention pertains to genetic markers which have a biochemically assayable (reporter) activity and confer a conditionally selectable growth advantage. The genetic markers are fused genes comprising a first structural gene which encodes the biochemically assayable product and a second, different structural gene which encodes a product whose activity confers the selectable growth advantage in a transformed cell. The translational product of the fused gene is a single contiguous polypeptide (fusion protein) which exhibits the activities of both gene products. In a preferred embodiment, the first structural gene encodes an enzyme that acts on a chromogenic substrate, such as the enzyme β-glucuronidase (GUS), and the second structural gene encodes an enzyme which confers antibiotic resistance to a transformed cell, such as the enzyme neomycin phosphotransferase (NPT-II) which confers resistance to several aminoglycoside antibiotics.

The genetic markers of this invention can be adapted for use in prokaryotic and eukaryotic cells, including yeast, animal and plant cells. They provide for powerful positive genetic selection and facile, sensitive biochemical and histochemical detection in transformed cells. They facilitate genetic selection of transformed cells and permit subsequent spatial localization and quantitative estimation of gene activity. In addition, the markers can be used to probe for and recover novel genes and genetic regulatory elements such as promoters.

DETAILED DESCRIPTION OF THE INVENTION

Figure 1:
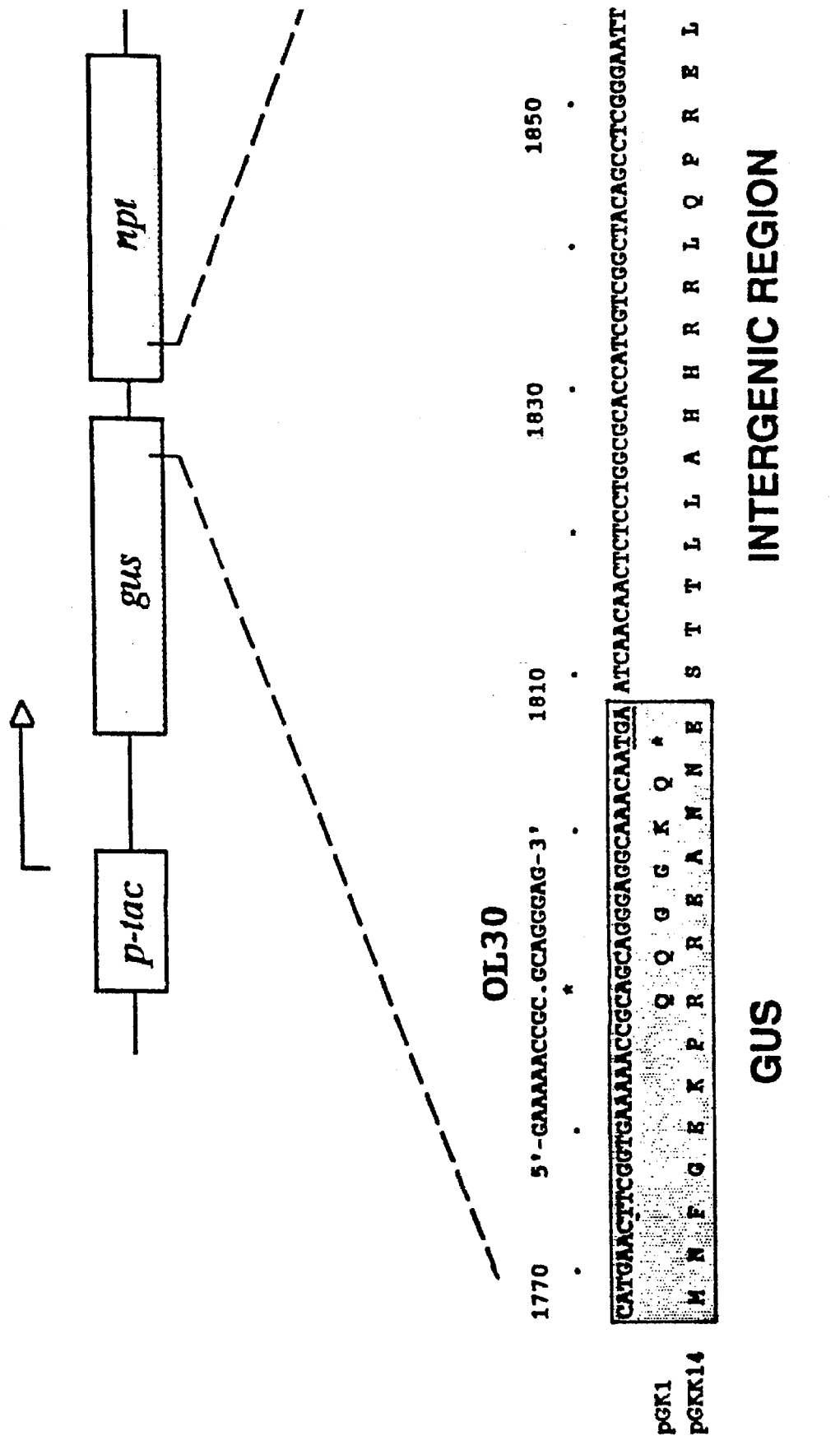
FIG. 1 is a schematic representation of a fusion between the carboxy-terminus of GUS and the amino-terminus of NPT-II.
Figure 1:
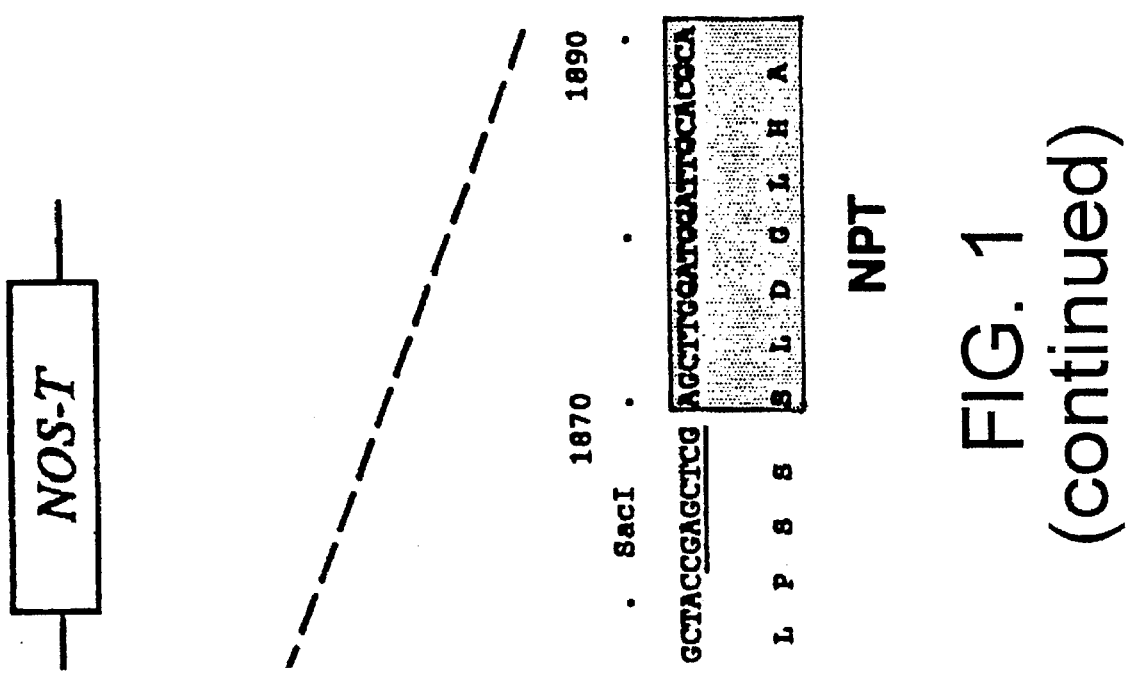

The genetic markers of this invention are bifunctional fused genes which provide a reporter activity and a trait which can be selected for. The fused genes comprise a first structural gene which encodes a product whose activity can be assayed bio-chemically fused to a second structural gene which encodes a product whose activity confers a growth advantage that is conditionally selectable.

The reporter gene preferably encodes an enzyme which acts on a chromogenic or luminogenic substrate. In general, the enzyme must have low enough activity in any prospective host cell so that the activity associated with the genetic marker can be distinguished from any endogenous (background) activity of the cell. Suitable enzymes may include GUS, chloramphenicol acetyltransferase (CAT), nopaline synthase (NOS), β-galactosidase (LAC) and luciferase (for example, firefly or bacterial luxAB luciferase).

The second gene of the fusion confers conditional growth advantage. This provides for positive genetic selection of cells transformed with the marker. The selectable trait can be antibiotic resistance, such as resistance to an aminoglycoside antibiotic (e.g. neomycin, kanamycin, hygromycin or gentamycin). Alternatively, genes which confer resistance to other types of antibiotics, such as CAT which confers resistance to chloramphenicol, can be used. In addition, the gene can be a modified or mutant gene. Some examples are a modified actin gene which confers resistance to bleomycin, the str gene which encodes an altered bacterial rRNA resulting in streptomycin resistance or the mdr gene which encodes a mutant membrane protein that confers multiple drug resistance.

A preferred embodiment of the marker is a gus::npt-II fusion gene. This marker is especially useful in plants. The gus gene (*E. coli* uidA) has all of the relevant features of a reporter gene for plants as well as other systems that lack significant endogenous GUS activity (Jefferson, *Plant Mol. Biol. Rep.* 5:387–405, 1987). It meets the criteria of sensitive and simple assayability—a low background of endogenous activity in plants, lack of toxicity in transgenic plants (Jefferson etal., *EMBO J.* 6:3901–3907, 1987) and the availability of convenient substrates such as the indigogenic substrate 5-bromo-4-chloro-3-indolyl-$\beta$-D-glucuronide (XGluc). GUS has been used as a biochemical and histochemical marker, alone or as a transcriptional reporter in studying developmental patterns of gene expression.

The npt-II gene provides resistance to the aminoglycoside antibiotics neomycin, kanamycin and geniticin. It is a widely used marker in several taxonomically diverse representatives of bacteria, fungi, plants and animals. Its broad host range, its ability to provide for positive genetic selection and the availability of a radiochemical assay for NPT-II contribute to the widespread use of the gene. The kanamycin-resistance ($Km^R$) phenotype conferred by the npt-II gene is the most prevalent selection marker in plant genetic transformation (Klee et al., *Ann. Rev. Plant Physiol.* 38:467–486, 1987) where it has also been used as a reporter in transcriptional and translational fusions (Teeri et al., *EMBO J.* 5:1755–1760, 1986; Vaeck et al., *Nature* 328:33–37, 1987). However, the use of the gene as a reporter has been limited because of the lack of an assay for NPT-II activity other than the radiochemical method (Radke et al., *Theor. Appl. Genet.* 75:685–694, 1988) or the less commonly used method of immunoscreening with polyclonal antibodies (Vaeck et al., *Nature* 328:33–37, 1987).

The component genes for constructing the markers of this invention can be obtained from standard sources or synthesized. The first and second structural genes can be fused together either directly or through an intergenic nucleotide sequence. The order of fusion can vary depending on the capability of a particular gene product to accept fusions at the carboxy- or amino-terminus. This capability can be determined empirically. A 5' location of the gene encoding the biochemically assayable enzyme, in relation to the gene conferring the conditionally selectable growth advantage, increases the likelihood that transformed cells selected for the growth advantage will also exhibit the reporter activity.

The genes can be fused by several different methods. One method is based upon the assumption that if stable fusions are possible between any two genes of interest, they will form and persist in vivo. A construct is prepared in which the coding region of the second gene is placed out of frame relative to the coding region of the first gene such that selection for function of the second gene will favor appropriate mutations for its expression.

As described in greater detail in the Exemplification below, this in vivo approach was taken to construct gus::npt-II fusions. The procedure is applicable to the fusion of other genes. Gene fusions were prepared in which the npt-II gene was placed out of frame with respect to an upstream gus gene. To prevent secondary translational initiation of the npt-II coding region, its initiation codon was removed. The fused gene was placed under the control of the tac promoter. The plasmid carrying this construct was phenotypically $GUS^+$ and $Km^S$ as the initial construct. *E. coli* cells were transformed with the plasmid and spontaneous bacterial mutants which had acquired kanamycin resistance were selected. Analysis of the nucleotide sequence of the fused gene at the junction region revealed that a single nucleotide had been deleted. close to the gus translational stop codon. This deletion brought the npt-II coding region into frame with the gus coding region but placed the original gus stop codon out of frame. Biochemical analysis showed the fusion protein was bifunctional having the enzymatic activities of the two individual genes.

In an alternative approach to constructing the gene fusions of this invention, the coding regions of the two genes can be fused together in proper frame and placed directly under the control of an appropriate promoter. To create these fusions, of course, the translational stop codon associated with the 5' structural gene must be inactivated so that translation will carry through to the coding region of the 3' structural gene. This can be accomplished by deleting the codon, changing it or by placing it out of frame by making an upstream nucleotide insertion or deletion, in conjunction with an appropriate downstream deletion or insertion which brings the coding region of the 3' structural gene into frame with the coding region of the first structural gene. In addition, the coding region of the 3' gene should be modified to remove or deactivate the initiation codon and any surrounding ribosomal binding sites to prevent secondary initiations. Positive gene fusions can be verified as described in the first approach.

In some cases, the fusionsprotein may be deleterious to cells. When this is the case, expression of the fusion gene can be regulated. For example, in *E. coli*, a lacI (repressor) gene can be used to regulate the expression of the fusion gene. Differential screening in the presence and absence of the tac-promoter inducer isopropylthiogalactoside can be used to assess deleterious expression.

The genetic markers of this invention have a wide spectrum of utility. They are useful in pro-karyotic and eukaryotic systems including yeast, other fungi and animal cells—generally any system for which gene-transfer protocols have been devised and where combinations of assayable and selectable marker genes can be usefully employed. The genetic markers of this invention simplify construction of nucleic acid vectors. The markers can be used in standard animal, plant and bacterial nucleic acid vectors. To activate the marker, it is operatively linked to a transcriptional promoter (and optionally an enhancer) which is active in the biological host of interest.

As described, the fused gene gus::npt-II is particularly useful as a marker in plants. It can be used in standard plant cell vectors such as Ti plasmids of *A. tumefaciens* in connection with a suitable transcriptional promoter active in plants. The marker gene allows selection at the whole plant level or callus stage. For instance, placed in combination with a constitutive promoter, the marker gene enables the selection of kanamycin resistant seedlings in progeny. In addition, the gus::npt-II marker allows direct kanamycin selection of transformed plant cells at the callus stage and subsequent enzymatic or histochemical assessment of the GUS activity in regenerated plants. The GUS activity of the marker can be employed to conveniently enzymatically correlate the expression of the marker with a kanamycin resistant phenotype. This is especially useful in recalcitrant species where the efficiency of genetic selection using aminoglycoside antibiotics is poor.

The genetic markers of this invention can also be used as molecular probes for genetic regulatory elements. They offer a powerful approach for the identification, characterization and recovery of these elements. As described below, the probes can insertionally tag active genetic regulatory elements such as transcriptional promoters in genomic or other DNA. These may include tissue-specific and developmentally specific regulatory elements.

In general, a probe for insertional tagging of a transcriptional promoter comprises a mobile genetic element, such as a plasmid, virus or a transposon, containing a genetic marker of this invention, without its own transcriptional promoter, located proximate to an insertion Junction of the element. The location of the marker next to an insertion junction allows it to be activated by a transcriptional promoter situated adjacent to the other side of the junction. Thus, insertion of the probe into a cellular genome will occasionally result in the genetic activation of the marker gene by its juxtaposition to a chromosomal regulatory sequence. The active regulatory element so identified can then be isolated by any of several recombinant DNA approaches.

Figure 7:
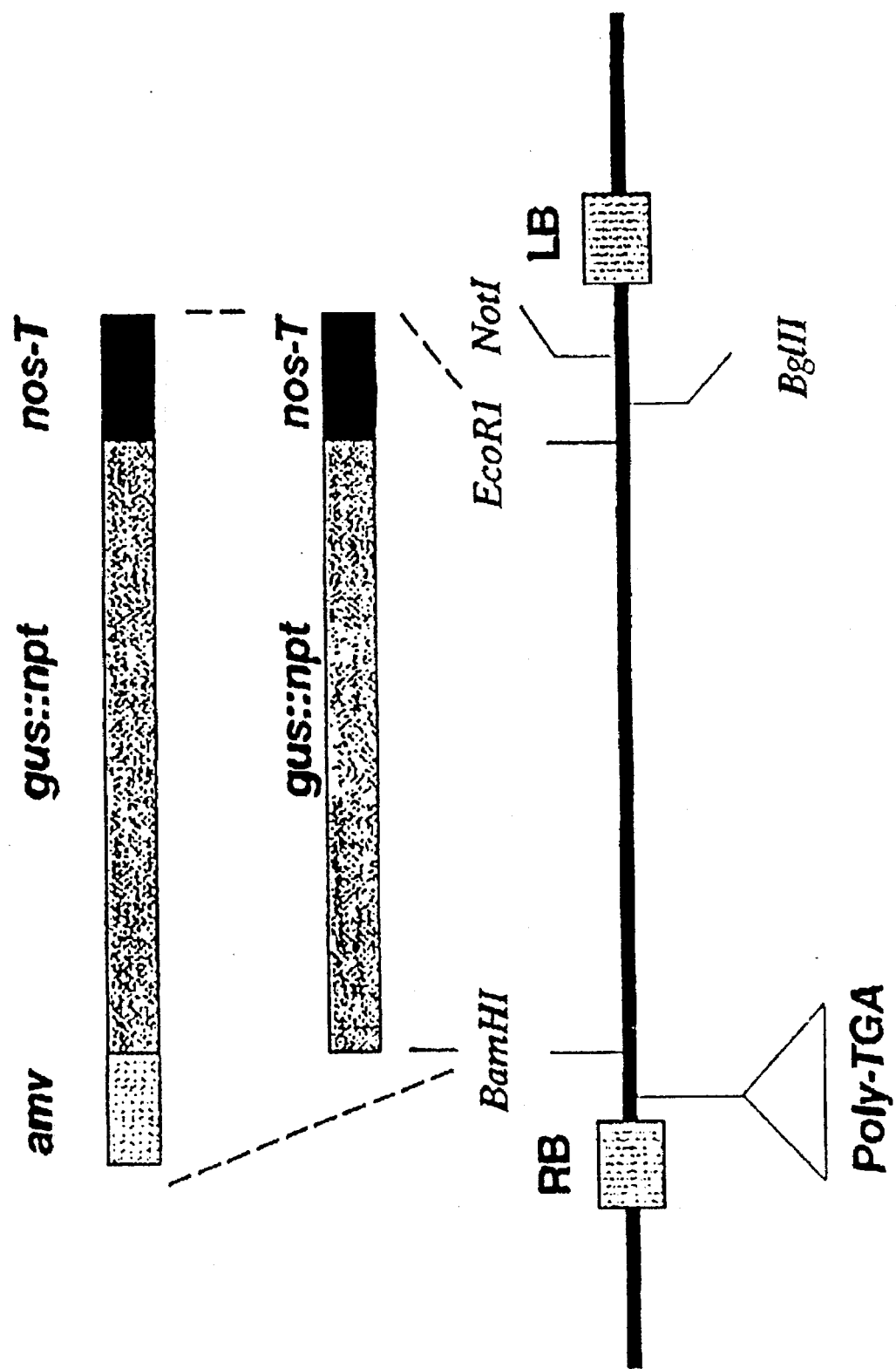
FIG. 7 is a schematic diagram of a probe designed for insertional tagging of plant promoters through T-DNA mediated transformation.

FIG. 7 shows a preferred embodiment of a probe designed for insertional tagging of plant transcriptional promoters through T-DNA mediated transformation. The probe contains the gus::npt-II fused gene located between the right border (RB) and left border (LB) Of the T-DNA. Preferably, the marker is located proximate to, and transcriptionally downstream from, the Ti right border sequence. A transcriptional terminator such as the transcriptional terminator sequence from the 3' region of the Ti nopaline synthetase gene (NOS-T) is placed 3' to the marker gene. A translational enhancer, such as the AMV enhancer shown, may be included between the border and the marker. Optionally, a sequence containing translational termination signals in all three reading frames (poly-TGA) can be located between the right border junction and the marker gene. This enables the exclusion of further peptide fusions upon insertion of the marker gene into a chromosomal or other gene. This arrangement serves to further specifiy the selection of transcriptional fusions exclusively, for purposes of identification of new regulatory sequences.

Upon integration of the probe into plant cellular DNA, activation of the gus::npt-II gene can be directly selected for on the basis of resistance to an aminoglycoside antibiotic such as kanamycin. Expression characteristics of the tagged regulatory sequence can be conveniently followed by assessment of GUS expression. In this way, the gus::npt-II gene can greatly facilitate the selection and characterization of plant genes which exhibit various expression patterns, the evaluation of regulatory elements in vivo and the determination of their activity through development.

The regulatory sequence identified by the insertional tagging procedure can be recovered by any of several approaches. Total genomic DNA can be isolated from transformed cells or tissues, cleaved with restriction enzymes and then submitted to Southern analysis using the gus::npt-II coding region or a portion thereof as a hybridization probe to identify fragments containing the marker gene. In this way, useful restriction enzyme sites upstream of the insertion junction of the probe can be approximately localized. Genomic DNA can then be cleaved with the cognate restriction endonuclease to generate restriction fragments which include the region upstream of the junction containing the regulatory sequence and some portion of the gus::npt-II sequence. The restriction fragment can then be subcloned and identified using an appropriate hybridization probe for the unique sequence associated with the retained portion of gus::npt-II.

Alternatively, a polymerase chain reaction (PCR) can be used to amplify the sequence. When necessary, in the event the chosen restriction site leaves a 3' recessed end, the restriction fragment can be bluntended (using a DNA polymerase in the presence of all four deoxynucleotides) and 'tailed' with oligo(dA) at its 3' terminus using terminal deoxynucleotidyl-tranferase. The PCR can then be performed with two primers: oligo(dT) and a gus-specific oligonucleotide complementary to the non-coding strand of 5' region of the gus gene. The amplified PCR product (by virtue of the specificity and orientation of the gus-specific primer) is the chromosomal region between the insertion junction and the site of oligo(dA) tail at the restriction enzyme site.

In yet another method, the restriction fragment can be circularized by self-ligation and then amplified by an "inverse" PCR. For this, diverging oligonucleotide primers are used. One is complementary to the non-coding strand in the 5' region of the gus::npt-II coding region; the other is complementary to the coding strand in the 3' region of the gus::npt-II coding region of the NOS polyadenylation sequence.

The regulatory sequence associated with the gus::npt-II probe can also be isolated by standard recombinant DNA methods. For example, a genomic library of the insertionally tagged cellular DNA (e.g. a genomic library of DNA purified from a regenerated plant) can be constructed. The library can be screened with a hybridization probe derived from the gus::npt-II coding region or from the transcribed, non-translated "leader" region immediately 5' to the insertion junction. This leader sequence can be determined by RACE-PCR cloning and sequencing of the specific gus::npt-II cDNA associated with the insertional tagging, using cDNA libraries generated from the tissue where the gus::npt-II marker gene is expressed.

In addition to the regulatory sequence, the gene naturally associated with the regulatory sequence can be isolated. The insertionally tagged DNA is cleaved with a convenient restriction enzyme to produce a restriction fragment which includes some portion of the region transcriptionally 'downstream' from the site of chromosomal insertion of the probe (for example the SacI site situated between the 3' terminus of gus::npt-II and the NOS-T polyadenylation sequence). The fragment can be subcloned using a hybridization probe specific for the carboxy-terminal region of the gus::npt-II marker as a probe for the gene.

A PCR procedure similar to that described above can also be used to isolate the gene. An oligo(dT) primer is used in combination with a gus::npt-II or NOS terminator-specific oligonucleotide primer complementary to the coding strand of 3' region of the gus::npt-II gene or NOS-T sequence. The amplified product, by virtue of the specificity and orientation of the gus::npt-II or NOS terminator-specific primer, will be the chromosomal DNA region between the 3' end of the gus::npt-II and the site of oligo-dA addition at the chosen restriction enzyme site.

The invention is illustrated further by the following exemplification.

Exemplification

The following abbreviations are used: Ap, ampicillin; bp, base pair(s); CaMV, cauliflower mosaic virus; DTT, dithiothreitol; GUS, β-glucuronidase; gus, E. coli gene encoding GUS (uidA); kb, kilobase(s) or 1000 bp; Km, kanamycin; NPT-II, neomycin phosphotransferase-II; npt-II, gene encoding NPT-II; nt, nucleotide(s); oligo, oligodeoxyribonucleotide; PAGE, polyacrylamide gel electrophoresis; PolIk, Klenow (large) fragment of E. coli DNA polymerase I; $^R$, resistance/resistant; SDS, sodium dodecyl sulfate; XGluc, 5-bromo-4-chloro-3-indolyl-β-D-glucuronide; ::, novel joint (fusion); [ ], denotes plasmid carrier state.

Assembly of gus::npt-II fusions in vivo and in vitro

Plasmid DNAs were prepared in large volume as described (Clewell and Helinski, *Biochemistry* 9:4428–4440, 1970), or using a minipreparation procedure (Ish-Horowicz and Burke, *Nucl. Acids. Res.* 9:2989–2998, 1981). Standard recombinant DNA techniques were used (Manjarls et al., Cold Spring Harbor Laboratory, Cold Spring Harbor, N.Y., 1982). A 0.8 Kb HindIII fragment containing the truncated npt-II structural gene from plasmid pABDI (Paszkowski et al., *EMBO J.* 3:2717–2722, 1984) was modified by filling-in with PolIk and by addition of an 8-mer SacI linker. The resulting SacI fragment was ligated into the corresponding site in pBI221 (Jefferson et al., *EMBO J.* 6:3901–3907, 1987) 3' to the gus gene. Lastly, the resident plant promoter element was replaced by a HindIII-BamHI fragment containing a 96 nucleotide (nt) bacterial tac promoter cassette (Pharmacia-LKB) to yield pGK1. Approximately $10^{11}$ cells of DH5α[pGK1] were plated on kanamycin-containing medium and some $10^3$ Km$^R$ colonies were recovered and pooled. DH5α was re-transformed with plasmid DNA from the pool, and colonies plated to ampicillin-containing medium. These were screened for Km$^R$ and some twenty were found to be doubly ampicillin and kanamycin resistant. Colonies were replica-plated and assayed for GUS overexpression on Whatman filter disks impregnated with a bacterial lysis solution (Holmes and Quigley, *Anal. Biochem*, 114:193–197, 1981) containing the indigogenic GUS substrate 5-bromo-4-chloro-3-indolyl-β-D-glucuronide (XGluc, Research Organics Inc.; Jefferson, *Plant Mol. Biol. Rep.* 5:387–405, 1987). The junction nucleotide sequence (determined by the procedure of Sanger et al., *Proc, Natl. Acad. Sci. USA* 74:5463–5467, 1977) of the fusion gene is shown in FIG. 1 within stippled boxes to indicate coding region domains derived from the gus and npt-II structural genes, and are separated by the 61 nt intergenic region originating from the 3'nontranslated sequence of *E. coli* uidA. (The nucleotide and amino sequence corresponding to the junction within pGKK14 are provided as Sequence ID No. 1 and 2 respectively. Likewise, the junction nucleotide and amino acid sequence within pGK1 are given as Sequence ID No. 3 and 4.) The gus termination codon and npt-II 5' SacI linker modification are underlined. Site-directed mutagenesis was carried out using the procedure of Kunkel, *Proc. Nat. Acad. Sci. USA* 82:488–492, (1985), with oligonucleotides synthesized using phosphoramidite chemistry on a Biosearch model 8700 synthesizer. Oligonucleotide OL30 (Sequence ID No. 5 in the Sequence Listing) is shown above the bold and asterisked 'A' nucleotide at position 1790, which is present in GK1 and deleted in the pBI-403A and pBI-403B site-directed mutants. The deduced amino acid sequence spanning the gus, intergenic and npt-II coding regions is shown as predicted for the parental GUS (Seq. ID No. 4) and fusion peptides (Seq. ID No. 2).

Figure 2A:
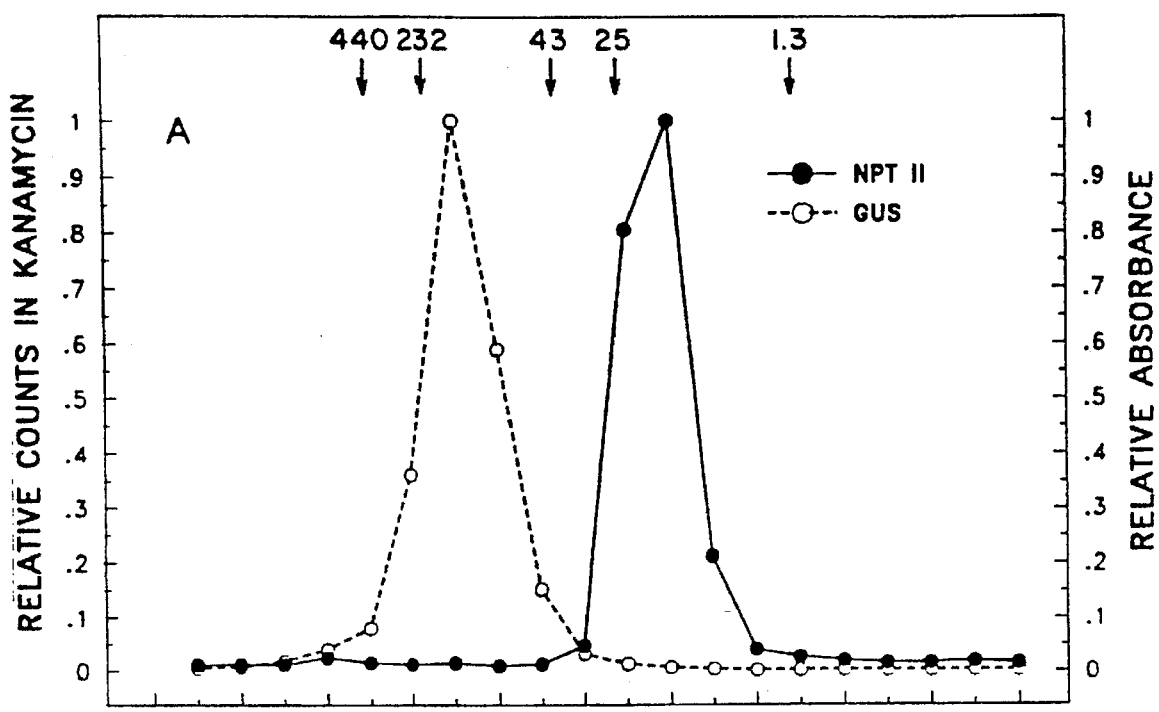
FIGS. 2A and B show the comigration of GUS and NPT-II activities in extracts of DH5α cells transformed with a plasmid carrying the gus::npt-II fused gene on molecular sieve chromatography.
Figure 2B:
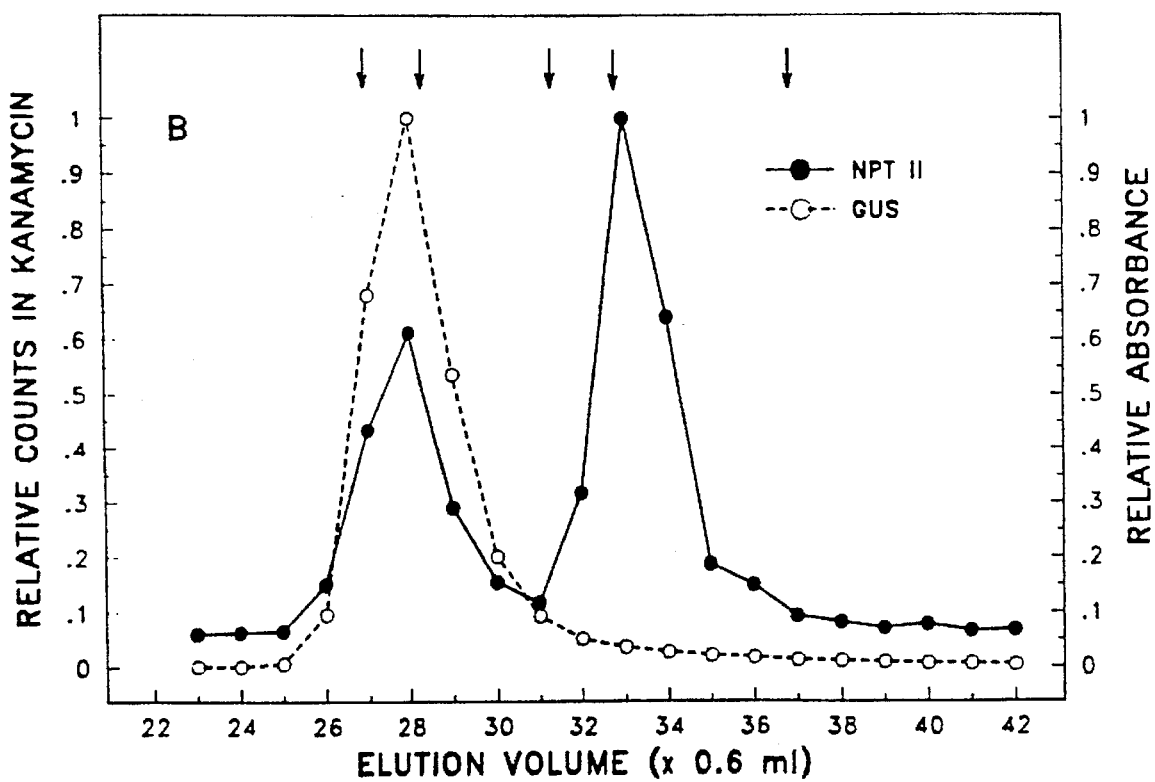

Molecular sieve chromatouraphy of native proteins from *E. coli* strains expressing gus, npt-II and gus::npt-II fusion genes All procedures were performed at 0°–4° C. For *E. coli*, mid-log phase cells (20 ml) were washed with an extraction buffer containing protease inhibitors as described (Platt and Yang, *Anal. Biochem.* 162:529–535, 1987) and resuspended in 1 ml. Cells were lysed in a pressure cell and the nucleic acids were removed by protamine sulphate precipitation (0.4% final concentration). 200 μl samples of these extracts were loaded onto a Superose 6 column (Pharmacia LKB) and the proteins eluted with a Tris-maleate/DTT buffer (67 mM Tris-maleate, 42 mM MgCl$_2$, 400 mM NH$_4$Cl, 5 mM DTT, pH 7.2). The NPT-II assays measured phosphorylation of kanamycin using a dot blot method to P81 paper essentially as described by Radke et al., *Theor. Appl. Genet.* 75:685–694, 1988. Spots were located by autoradiography and activities were quantified by excising radioactive P81 spots and counting in a universal liquid scintillation cocktail (Scintiverse-II; Fisher Scientific). GUS activity was measured spectrophotometrically using p-nitrophenyl-β-D-glucuronide as substrate, or by histochemical localization as described (Jefferson, *Plant Mol. Biol. Rep.* 5:387–405, 1987). Panel A of FIG. 2 shows a chromatogram for strain DH5α carrying plasmids pGK1 and pGS39, expressing gus and npt-II respectively. Panel B shows a chromatogram for strain DH5α carrying pGKK14, which has the fused gus::npt-II gene. The column was calibrated with size standards (Pharmacia or BioRad) and sizes in kilodaltons are shown by the arrows: 440, ferritin; 232, catalase; 43, ovalbumin; 25, chymotrypsinogen A; 1.3, vitamin B12. Protein concentrations were determined as described (Jefferson et al., *Proc. Nat. Acad. Sci. USA* 83:8447–8451, 1986). The relative values of 1 in Panel A correspond to 116,816 cpm (NPT-II assay) and an OD$_{415}$ of 3.25 (GUS assay, inclusive of a multiplication factor for absorbance); Panel B values were 17,424 cpm (NPT assay) and OD$_{415}$ 1.24 (GUS).

Immunoblot analysis of *E. coli*-produced GUS and GUS::NPT-II fusion proteins

Figures 3A, 3B:
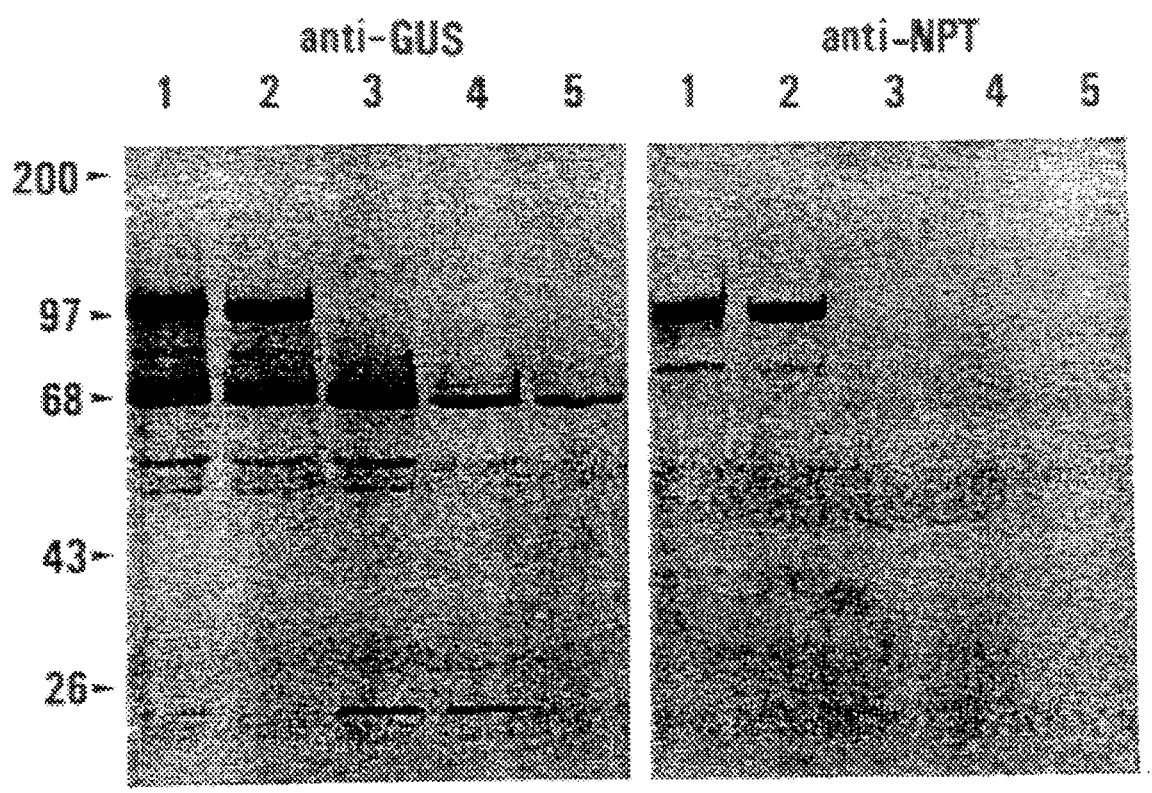
FIGS. 3A and B show immunoblot analysis of E. coil-produced GUS and GUS::NPT-II fusion proteins.

Extracts from *E. coil* were denatured and electrophoresed in a 0.1% SDS 7.5% PAGE (SDS-PAGE; Laemmli, *Nature* 277:680–685, 1970) before electroblotting to nitrocellulose membranes (Burnette, A. *Anal. Biochem.* 112:195–203, 1981). Protein estimations employed the dye-binding method (Bradford, *Anal. Biochem.* 72:248–254, 1976). The blots were screened for immunoreactive bands with polyclonal antibodies against GUS (Clontech, San Francisco) or NPT-II (5'-3' Inc., Cleveland) using goat anti-rabbit alkaline phosphatase conjugate as secondary antibody (ProMega Biotec, Madison). FIG. 3 shows the immunoblots. Lane 1, DH5α[pBI-403A]; 2, DH5α[pBI-403B]; 3, DH5α[pGK1]; 4, DH5α; 5, 10 ng purified GUS. Size markers used were from BRL Life Technologies (not shown) and are indicated in kilodaltons.

Gel permeation chromatography of plant extracts

Figure 4A:
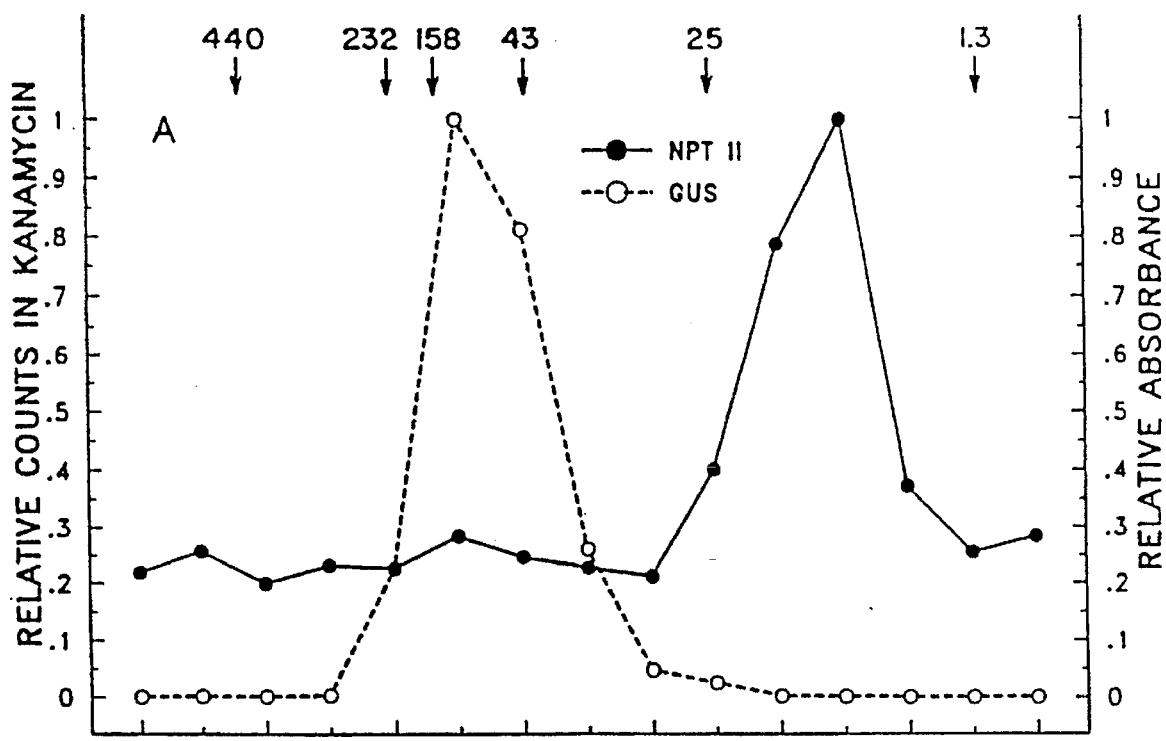
FIGS. 4A and B show the elution profile of GUS and NPT-II activity in extracts of tobacco plants transformed with a plasmid carrying the gus::npt-II fusion gene on gel permeation chromatography.
Figure 4B:
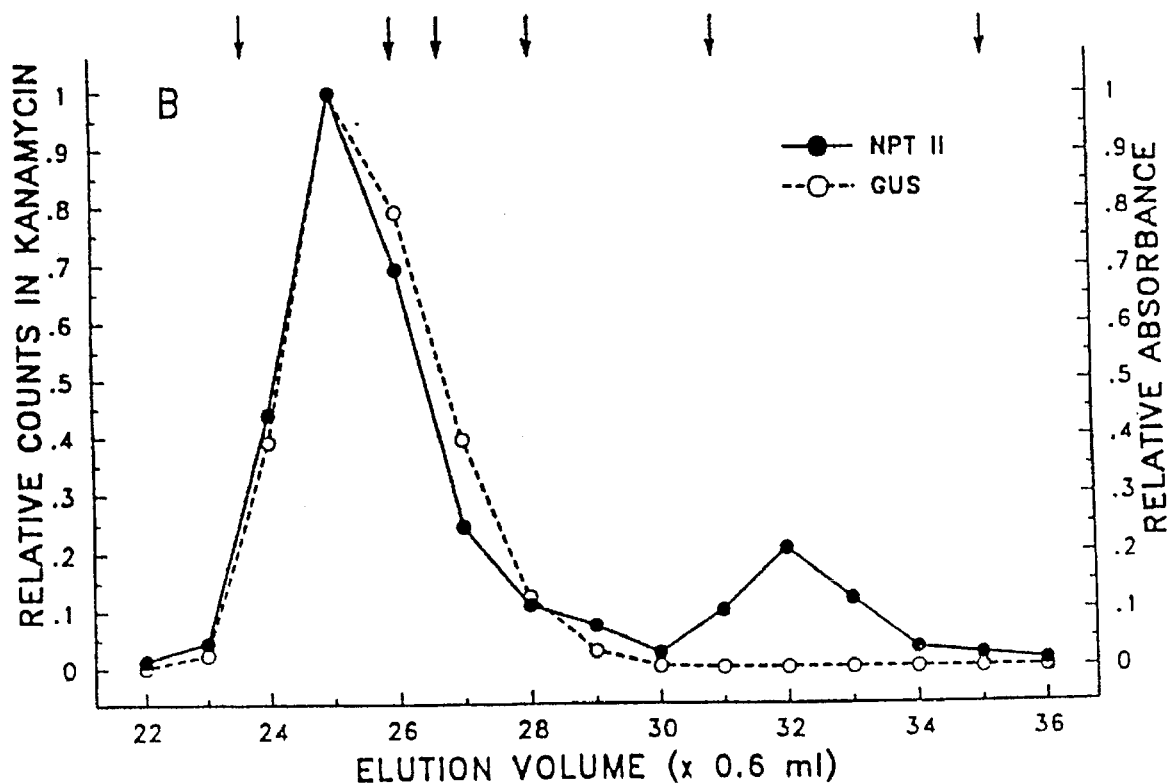

Gel permeation chromatography was performed on extracts (A) from transgenic plants expression gus and npt-II from two independent promoters within a disarmed T DNA, or (B) from a single promoter as a fused gene product. The bifunctional GUS::NPT-II fusion gene generated in *E. coli* was fused to a HindIII-BamHI CaMV 35S transcript promoter fragment from pBI221 (Jefferson et al., *EMBO J.* 6:3901–3907, 1987) and cloned into pMON806 resulting in pBI405. pMON806 (the kind gift of Dr. Harry Klee, Monsanto Co., St. Louis, Mo.) is an *Agrobacterium tumefaciens* binary plasmid which incorporates a methotrexate resistance marker selectable in plants, but which lacks plant-selectable npt-II or gus genes. This construct was transferred by conjugation to *A. tumefaciens* strain MP90 (Koncz and Schell, *Mol. Gen. Genet.* 204:383–396, 1986), and used in transforming tobacco leaf disc explants as described (Hotschat et al., *Science* 277:1229–1231, 1985). Plant extracts were prepared from 0.5 g of leaf material from a young plant was ground to a fine powder in liquid nitrogen with 0.125 g of polyvinylpolypyrrolidone and extracted with 50 μl of β-mercaptoethanol and 250 μl of buffer containing 100 mM Tris-HCl/0.1% sodium dodecylsulfate/1 mM phenylmethylsulfonylfluoride/5 mM DTT, pH 7.4. The extract was centrifuged at 20,000×g for 30 min and 200 µl of the supernatant was loaded on a Superose 6 column. The proteins were eluted and the enzymes were assayed as described (Jefferson, *Plant Mol. Biol. Rep.* 5:387–405, 1987; Jefferson et al., *EMBO J.* 6:3901–3907, 1987). The chromatograms are shown in FIG. 4. Size standards were the same as for FIG. 2, except aldolase (158 kDa) was also included. The slight shift in elution volumes is due to the use of independent columns. The relative values of 1 for NPT-II and GUS assays in Panel A correspond to 2,000 cpm and an absorbance of 7.68 respectively. Panel B, 39,255 cpm (NPT-II) and 3.67 (GUS).

Immunodetection of GUS and NPT polypeptides in extracts from transgenic tobacco

Figures 5A, 5B:
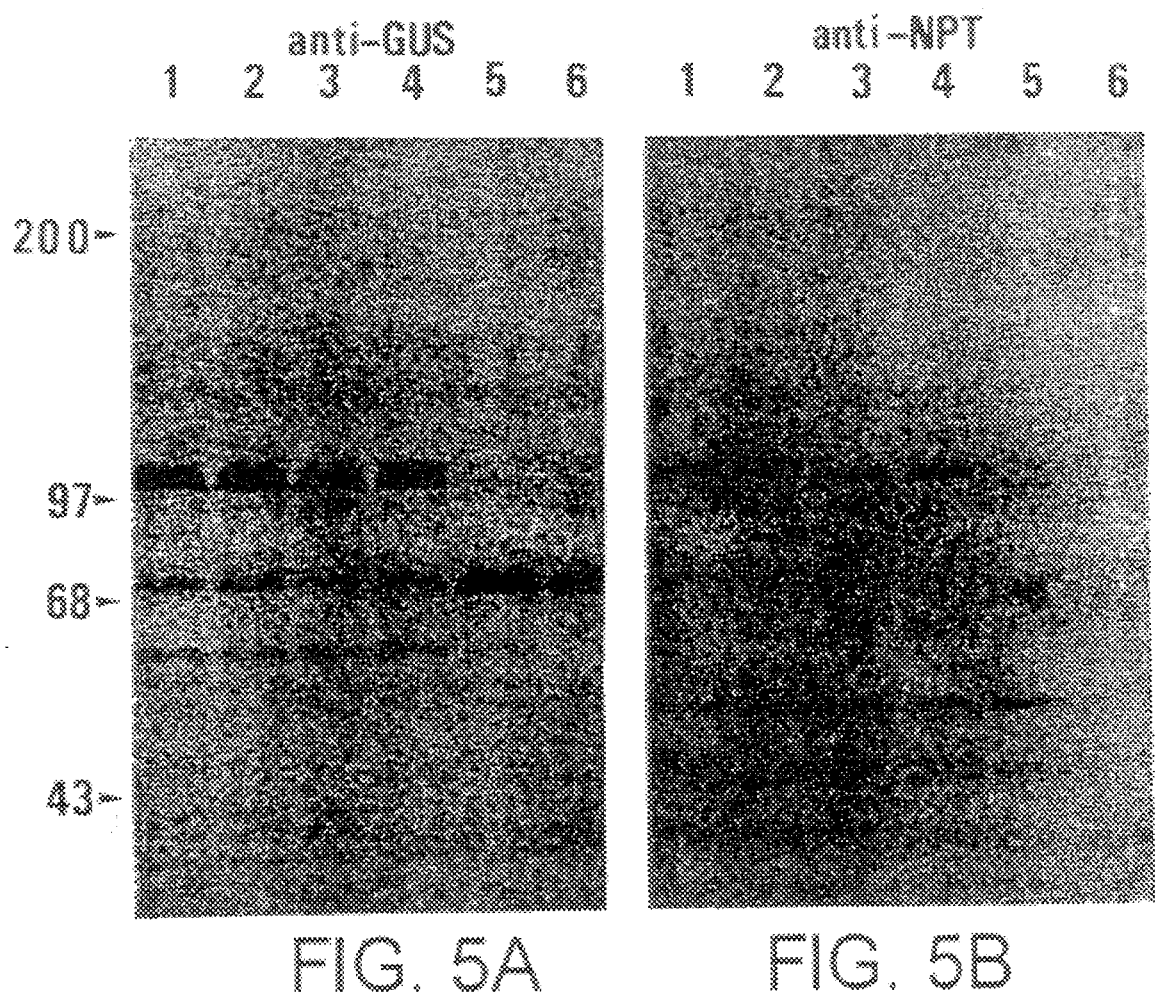
FIGS. 5A and B show the immunodetection of GUS and NPT-II polypeptides in leaf extracts from the transgenic tobacco plants.

Plant extracts were prepared as described above. The immunoblot is shown in FIG. 5. Lanes 1–4, transgenic plants for the GUS::NPT-II fusion; 5, transgenic for independently expression GUS and NPT-II; 6, 10 ng purified *E. coli* GUS.

Activity gel assay of GUS in transgenic tobacco

Tobacco protein extracts were prepared as described above with the addition of 10 µg/ml leupeptin (Sigma) to the extraction buffer. Aliquots containing 100 µg of protein were incubated in 1× SDS reducing buffer at 37° C. for 2 minutes, and resolved in a 0.1% SDS 7.5% PAGE gel (Laemmli, *Nature* 277:680–685, 1970). Gels were incubated in 0.5mg XGluc per ml, 0.05% $NaN_3$ as described (Jefferson et al., *Proc. Nat. Acad. Sci. USA* 83:8447–8451, 1986). FIG. 5 is a gel showing GUS activity. The GUS activity was visible as insoluble indigo precipitates in the gel matrix. Lane 1, plant transgenic for the gus::npt-II fusion gene in pBI-405; lane 2, plant transgenic for native gus from pRJ221 (Jefferson, *Plant Mol. Biol. Rep. 5:387–405, 1987*); lane 3, purified GUS.

Assembly of a gene encoding both gus and npt activities

The experimental design for generating fusions between the C-terminus of GUS and the N-terminus of NPT-II is illustrated in FIG. 1. While protein fusions to the amino-terminus of both GUS and NPT-II have been reported, NPT-II has been shown refractory to carboxy-terminal fusions (Reiss et al., *EMBO J.* 3317–3322, 1984). Since there existed no precedent for fusions at the C-terminus of GUS, an invivo approach was used to generate such fusions on the assumption that if stable fusions in the $NH_2$-GUS::NPT-COOH configuration were possible, they would form and persist in vivo. The gus coding region expressed from an upstream tac promoter was ligated to a npt-II coding region (Beck et al., *Gene* 19:327–336, 1982) that was deleted for the first four codons, including the initiation codon. This arrangement provided a functional gus gene with a termination codon, a gus-derived 3' non-translated "intergenic" region of 61 nt, followed by the truncated coding region of npt-II out of frame to the gus gene (see FIG. 1 and Sequence Listing). Attempts to maintain this construct pGK1 (and its derivatives) in the *E. coli* gus deletion mutant strain SO200 (Jochimsen et al., *Mol. Gen. Genet.* 143:85–91, 1975) were unsuccessful due to an unexplained high frequency of plasmid loss under non-selective conditions, and therefore DH5α was used for all subsequent studies. The multicopy plasmid pGK1 afforded overproduction of GUS in *E. coli* strain DH5α but did not confer kanamycin resistance on the host (data not shown). This indicated that there was no spurious transcription and/or translation of the npt-II coding region culminating in kanamycin resistance in vivo.

Since spontaneous genetic deletions are not uncommon, we anticipated to generate in-frame fusions between GUS and NPT-II in pGK1 as a rare but identifiable $Km^R$ event among a large number of $Km^S$ bacterial cells harboring the plasmid. This approach would also provide a solution in the event of transcriptional termination of gus at or before the intergenic region in pGK1. A further assumption was that only the stable fusion events or those which precisely cleaved the fusion peptide to its component npt-II domain would persist. To confine our further experiments to those that expressed a plasmid-associated $Km^R$ phenotype, we isolated plasmid DNA from the pooled $Km^R$ colonies ($10^3$ obtained from $10^{11}$ cells) and re-transformed DH5α, selecting for the ampicillin resistance marker associated with the vector component of pGK1. The $Ap^R$ colonies were replica-plated for $Km^R$ and $GUS^+$ phenotype as scored by filter assay. The overproduction of GUS was further confirmed by enzymatic assay of crude cellular extracts of 15 $Ap^R$ $Km^R$ $GUS^+$ clones (data not shown). Two such clones (pGKK7 and pGKK14) were then chosen to investigate the molecular basis of the $GUS^+$ $NPT-II^+$ phenotype.

Molecular basis of the gus::npt-II fusion and reconstruction of the fusion in vitro The region surrounding the junction of gus and npt-II in pGKK7 and pGKK14 was sequenced and compared to that in the parental plasmid, pGK1 (FIG. 1). DNA sequencing was initially limited to approximately 80 nt on both sides of the gus stop codon on the assumption that the TGA (underlined in FIG. 1) would have to be removed from the reading frame by a mutation in the triplet or by an upstream frame-shift. A further assumption was that such a frame-shift, if present, would be closer to the original stop codon in order to retain GUS activity. Likewise, wise, any lesions in the npt-II coding region would not likely extend too far into the gene. The results revealed a single base pair deletion near the 3' end of the gus coding region (A:T, bold type and asterisked at position 1790 in FIG. 1; nt 2089; Jefferson et al., *Proc. Nat. Acad. Sci. USA* 83:8447–8451, 1986). The relevant segments of the reading frames are shown in FIG. 1 and indicates this deletion would frameshift the TGA codon of gus and place the npt-II coding region in-frame to gus. Thus, the deletion in pGKK7 and pGKK14 was predicted to encode a fusion polypeptide of 885 amino acids encompassing the gus, intergenic and npt-II coding region domains.

The in vivo experiments and subsequent partial sequenced analysis of pGKK7 and pGKK14 did not exclude the possibility of additional mutational events elsewhere on pGK1. To determine that the only relevant change was the deletion of the A:T pair at position 1790, and that it alone was sufficient to confer $GUS^+$ and $Km^R$ phenotypes, the predicted mutational event was reconstructed from pGK1 by site-directed mutagenesis with an 18-met oligonucleotide (OL30; FIG. 1 and Seq ID No. 5). Of 100 $amp^r$ colonies analyzed, approximately 70% were $Km^R$ in subsequent screening and two such randomly chosen clones, pBI-403A and pBI-403B, were resequenced and shown to contain the predicted A:T deletion (data not shown). These experiments confirmed our interpretation of the in vivo experiments with regard to the genetic basis of the GUS::NPT-II protein fusion, and the functional equivalents of pBI-403A/B with pGKK7 and pGKK14.

Biochemical and immunological evidence for bifunctional GUS::NPT-II protein

Crude extracts of DH5α[pGKK14] were fractionated by molecular sieve chromatography. The results shown in FIG. 2 indicated co-migration of all of the GUS activity with approximately 40% of the total NPT-II activity in the extract. The remainder of the NPT-II activity was found in a slowermigrating peak. The control extract from a strain expressing GUS from the parental plasmid pGK1, and NPT-II in trans from a second plasmid pGS39 (derived from pGS38; Selvaraj and Iyer, *J, Bacteriol.* 158:580–589, 1984) resolved into two distinct peaks containing independently the GUS and NPT-II activities, effectively ruling out the possibility of a spurious post-translational association of NPT-II and GUS subunits into a quaternary complex. The apparent sizes for these classes of proteins were estimated at 270 kDa for the fusion peak and 25 kDa for the NPT-II peak in the same extract, compared with the control values of 140 kDa and 20 kDa for the unfused GUS and NPT-II respectively. The 25 kDa protein in the fusion extract may result from secondary translation from an in-frame ATG found at position 1768 with its attendant ribosome binding site-like sequence 5 nt upstream (nt 2067; Jefferson et al., *Proc. Nat. Acad. Sci. USA* 83:8447–8451, 1986). However, since anti-NPT-II polyclonal antibodies failed to identify a discrete NPT-II polypeptide of lower molecular weight in sonicated extracts (see below and FIG. 3), this fraction of NPT-II activity is more likely the result of general proteolytic degradation arising from extended handling of samples for column chromatography. Notwithstanding, this property of the GUS::NPT-II protein in *E. coli* does not detract from its usefulness as discussed below. This constituted evidence for a protein fusion and suggested that the native *E. coli* GUS may be active as a homodimer. Further evidence for expression of the fusion was obtained by immunoblot analysis of expressed polypeptides in DH5α carrying the relevant plasmids.

Immunoblot blot analyses ef protein extracts from DH5α, DH5α[pGK1] and DH5α[pGKK14] using polyclonal antibodies against GUS or NPT-II enzymes showed the presence of the fusion peptide exclusively in pGKK14-containing strains (FIG. 3). The estimated size for the fusion polypeptide of 96 kDa corresponds closely to the sum of GUS (68 kDa; Jefferson et al., *Proc. Nat. Acad. Sci. USA* 83:8447–8451, 1986) and NPT-II (25 kDa, Horsch et al., *Science* 227:1229–1231, 1985). These analyses also showed the presence of discrete smaller antigenic peptide fragments, suggesting some degradation of the GUS polypeptide and the fusion derivative. Activity gels with MUG as the substrate (Jefferson, *Plant Mol. Biol. Rep.* 5:387–405, 1987) showed GUS activity in bands of higher $M_r$ than the parental GUS, thus confirming the independent gel filtration and immunoblot experiments (data not shown; see FIG. 6 for a related experiment).

Taken together, the DNA sequence analysis, the co-purification on gel filtration columns of GUS and NPT-II activities as a single protein of predicted fusion molecular weight and the Western analysis argue in favor of expression of a bifunctional fusion gene and peptide in the $NH_2$-GUS::NPT-II-COOH configuration.

Expression of the GUS::npt-II bifunctional gene in plants

An objective of this study was to construct a versatile biochemical and genetic marker for simultaneous selection and screening in transgenic plants using the gus and npt-II genes. The utility of the bifunctional protein was tested in plants by transforming *Nicotiana tabacum* with pBI405 carrying the gus::npt-II chimeric gene (FIG. 4) in combination with the 35S transcript promoter from CaMV. Of 32 transgenic plants selected directly for $Km^R$, 28 were found to be GUS+ and in those plants tested, both markers were inherited as a single dominant locus through meiosts. While each positive plant exhibited GUS activity well above the control (plants transgenic for npt-II alone), there was variation in the GUS specific activity among individuals. Such variation could also be seen when plants were transformed with a non-fusion gus marker from pBI121 (data not shown; Jefferson et al., *EMBO J.* 6:3901–3907, 1987). Similar differences in gene activity among individual transgenic plants have been attributed to chromosomal position effects (Weising et al., *Ann, Rev. Genet.* 22:421–478, 1988).

Protein extracts from two independent GUS+ $Km^R$ plants were again subjected to gel filtration (FIG. 4) and immunoblot analyses (FIG. 5). The protein eluting at about 270 kDa contained both GUS and NPT-II activities, in contrast to the control plants where the proteins were expressed from independent promoters and the size of the unfused GUS was around 140 kDa. Interestingly, the bifunctional protein appeared to chromatograph as a trimer in both *E. coli* and tobacco although, in the absence of sedimentation coefficient data, such chromatographic behavior may merely reflect an exaggerated anisometry of the fusion peptide as a dimer. Alternatively, this difference may be due to the modified carboxy terminus of GUS in the fusion protein—an observation that is reminiscent of the different oligomeric structures of β-galactosidase mutants in *E. coli* (Fowler and Zabin, *Science* 154:1027–1029, 1966). It would be informative to dissect the functional domains of GUS and NPT-II from a practical viewpoint as well as with regard to studying the structure-function relationships of the two catalytic domains—particularly as it relates to a novel fusion between two proteins of different native quaternary structures. Unlike protein extracts from *E. coli* expressing the GUS::NPT-II fusion gene under the control of a tac promoter, only 10% of a smaller NPT-II protein was observed in transgenic plants expressing the fusion (see Panel B in FIGS. 2 and 4). Detection of GUS and NPT-II epitopes in a >97 kDa polypeptide fraction confirmed expression of GUS::NPT-II as a fusion protein in transgenic leaf tissues, and indicated a relative stability of the protein in these plants (FIG. 5). Since translation of polycistronic mRNA is limited to viral and organellar messages in plants (Bonneville et al., *Mosaic Virus Cell* 59:1135–1143, 1989); Angenon et al., *Molec. Cell. Biol.* 9:5676–5684, 1989), we surmise that the smaller NPT-II protein represents a product of the fusion and not a result of reinitiation within the gus::npt-II mRNA. Thus, the $Km^R$ phenotype can be manifested only upon expression of the intact GUS::NPT-II fusion peptide.

Figure 6:
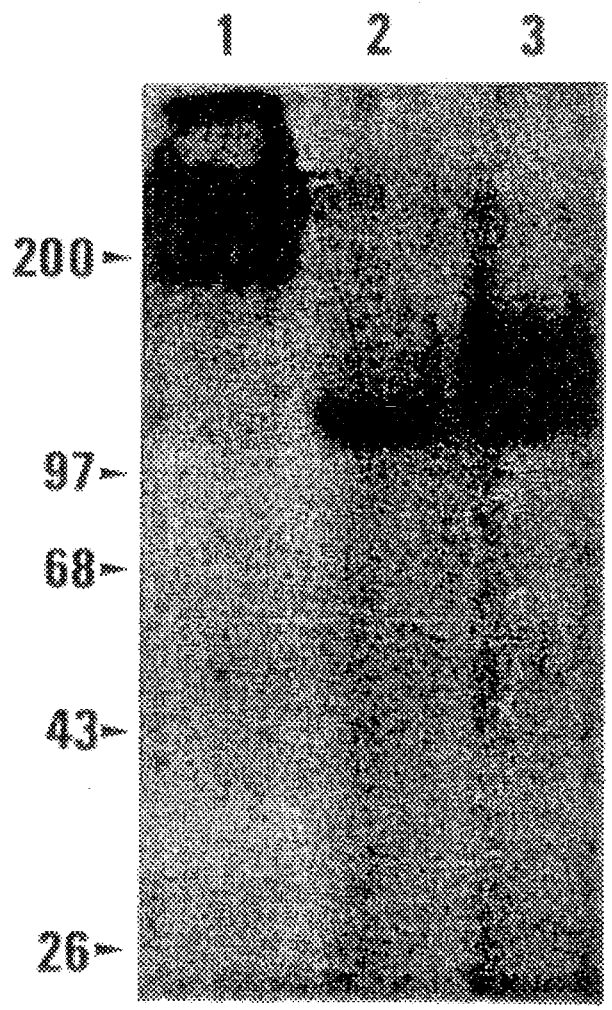
FIG. 6 shows gel electrophoretic analysis of GUS activity in tobacco plants.

Attempts were made to obtain zymograms using XGluc as the substrate for both unfused or fused GUS after SDS-PAGE of leaf extracts in a 7.5% gel (FIG. 6). Incubation of the samples in a loading buffer (Jefferson et al., *Proc. Nat. Acad. Sci. USA* 83:8447–8451, 1986) at 37° C. for 2 min prior to electrophoresis showed one prominent larger activity band for the fusion at >200 kDa position and a smaller one for the unfused GUS (and the purified GUS) at >97 kDa. Prolonged incubation at 37° C. abolished the GUS activity, although a polypeptide of predicted size could be seen under these conditions as shown in the immunoblots of FIG. 5. We surmise that under experimental conditions permissive for retaining the activity, the protein is not dissociated to yield subunits as reflected in the overall slower migration (FIG. 6). Thus, the results shown in FIGS. 4–6 clearly indicate stable expression of the bifunctional protein in plants.

Histochemical analysis of transgenic tobacco plants generated using the gus::npt-II fusion gene for selection showed patterns of expression similar to 35S promoter-driven gus constructs (Jefferson et al., 1987). The gus::npt-II fusion gene has been similarly used to generate transgenic plants of *Brassica napus* and *Arabidopsis thaliana*, and fusion-based plasmid constructs have been successfully employed in assays of transient gene expression in electroporated protoplasts of tobacco, White Spruce (*Picea glauca*) and maize.

Analysis of Transgenic Plants

Figure 8:
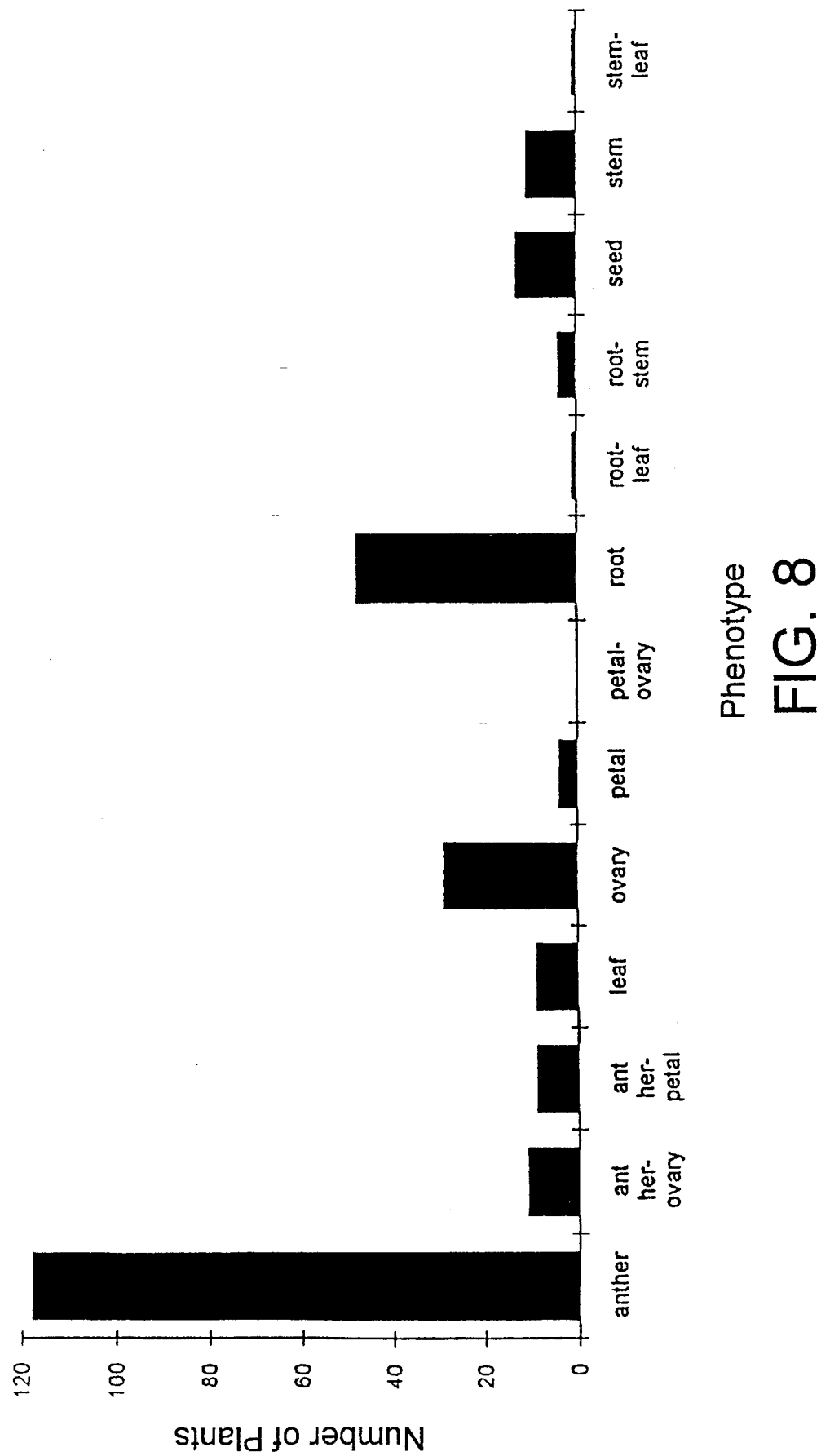
FIG. 8 is a histogram detailing tissue and/or developmental specific β-GUS expression.

Analysis of 1000 transgenic plants arising from the use of the gus::npt-II fusion gene was performed, and the results graphically summarized as a frequency histogram in FIG. 8. This study identified 243 plants which expressed some degree of tissue and/or developmental specificity of β-GUS expression. FIG. 8 indicates a 24-precent frequency of tissue-specific phenotypes and is in close agreement with previous results from analysis of a group of 200 transgenic plants (results not shown). All singular tissue-specific phenotypes sought (anther, leaf, ovary, petal, root, seed, stem) were found. In addition, most binary combinations of flower or somatic tissue-specificity were identified, including [anther+ovary], [anther+petal], [root+leaf], [root+stem] and [stem+leaf]. Only one binary flower tissue combination was not identified, [petal+ovary].

Assembly of a lux::npt Bifunctional Fusion Gene

The construct is based upon the gus::npt bifunctional fusion maker gene described above.

A near full-length coding region of the firefly (*P. pyralis*) luciferase gene was defined and amplified from a comercially available plasmid (pLUC; Promega, Madison Wis.) using PCR and oligonucleotides BC175 (Sequence ID No. 6) and BC176 (Sequence ID No. 7). This region was substituted for the NcoI-SacI GUS domain of the gus::npt bifunctional construct, thus generating the lux::npt combination. The complete nucleotide sequence of the chimetic lux::npt gene is given in Sequence ID No. 8, along with its corresponding deduced amino acid sequence in Sequence ID No. 9. This construct was used to transform *E. coli* cells, initially selecting for the expression of kanomycin resistance from the downstream npt domain. Kanomycin-resistant colonies were cultured and extracts assayed qualitatively for the expression of light-emitting activity using a liquid scintillation counter and a commercial assay kit (Promega, Madison Wis.). Among 4 colonies, three were positive for luciferase activity.

Equivalents

Those skilled in the art will recognize, or be able to ascertain using no more than routine experimentation, numerous equivalents to the specific procedures described herein. Such equivalents are considered to be within the scope of this invention and are covered by the following claims.

---

We claim:

1. A fused gene, comprising a first structural gene which encodes beta-qlucuronidase activity, fused in frame and linked by an intergenic nucleotide. sequence to a second structural gone which encodes neomycin phosphotransferase-II activity, and in a suitable host is capable of expressing a single, stable polypeptide translation product simultaneously having the combined activities of the first and second structural genes.

2. The fused gene of claim 1, wherein the first structural gens is fused to the 5' end of the second structural gens.

3. The fused gene of claim 2, wherein the beta-glucuronidase gene is attached at its 3' end to the 5' end of the intergenic nucleotide sequence.

4. A nucleotide which comprises beta-glucuronidase and neomycin phosphotransferase-II structural genes fused in frame and linked by an intergenic nucleotide sequence, wherein the nucleotide encodes and, in a suitable host is capable of expressing a single stable polypeptide translation product having both beta-glucuronidase and neomycin phosphotransferase-II activities.

5. The nucleotide of claim 4 wherein the neomycin phosphotransferase-II gene is attached at its 5' end to the 3' end of the intergenic nucleotide sequence.

6. The nucleotide of claim 5, wherein the beta-glucuronidase gene is attached at its 3' end to the 5' end of the intergenic nucleotide sequence.

7. A nucleic acid vector containing the nucleotide of claim 4, under regulation of a promoter.

8. The vector of claim 7, which is a plasmid.

9. A Ti plasmid containing a plant promoter and the nucleotide of claim 4.

10. A probe for a genetic regulatory element, comprising a mobile genetic element selected from the group consisting of a plasmid, a virus and a transposon, containing the nucleotide of claim 4.

11. The probe of claim 10, wherein the mobile genetic element is a T-DNA of a Ti plasmid, and the insertion junction is the T-DNA border of the Ti plasmid.

12. A probe for a plant promoter comprising a Ti plasmid containing a promotorless marker gene comprising, the nucleotide of claim 4, located proximate to the right (5') T-DNA border of the Ti plasmid.

13. The probe of claim 12, wherein a sequence containing translational termination signals in all three reading frames is located between the right border and the marker gene.

14. The probe of claim 12, further comprising a translational enhancer located between the marker gene and the T-DNA border.

15. The nucleotide of claim 4, wherein the intergenic nucleotide sequence is the 61 nt intergenic region originating from the 3' nontranslated sequence of *E. coli* uidA.

* * * * *

UNITED STATES PATENT AND TRADEMARK OFFICE
CERTIFICATE OF CORRECTION

PATENT NO. : 5,639,663
DATED : June 17, 1997
INVENTOR(S) : W. L. Crosby et al

It is certified that error appears in the above-indentified patent and that said Letters Patent is hereby corrected as shown below:

In the Claims, claim 1, line 4 "structural gone which" should read -- structural clone which--.

Signed and Sealed this

Seventeenth Day of March, 1998

*Attest:*

BRUCE LEHMAN

*Attesting Officer*   Commissioner of Patents and Trademarks